(12) United States Patent
Craigo

(10) Patent No.: US 12,042,503 B2
(45) Date of Patent: Jul. 23, 2024

(54) COMPOSITIONS AND METHODS FOR TREATING CORONAVIRUS INFECTIONS

(71) Applicant: CytoAgents, Inc., Pittsburgh, PA (US)

(72) Inventor: Jodi Craigo, Cranberry Township, PA (US)

(73) Assignee: CytoAgents, Inc., Pittsburgh, PA (US)

(*) Notice: Subject to any disclaimer, the term of this patent is extended or adjusted under 35 U.S.C. 154(b) by 0 days.

(21) Appl. No.: 17/174,423

(22) Filed: Feb. 12, 2021

(65) Prior Publication Data

US 2021/0244746 A1 Aug. 12, 2021

Related U.S. Application Data

(60) Provisional application No. 63/057,095, filed on Jul. 27, 2020, provisional application No. 63/020,342, filed on May 5, 2020, provisional application No. 62/975,369, filed on Feb. 12, 2020.

(51) Int. Cl.
*A61K 31/5585* (2006.01)
*A61K 9/00* (2006.01)
*A61K 45/06* (2006.01)
*A61P 31/14* (2006.01)

(52) U.S. Cl.
CPC ........ *A61K 31/5585* (2013.01); *A61K 9/0053* (2013.01); *A61K 45/06* (2013.01); *A61P 31/14* (2018.01)

(58) Field of Classification Search
CPC ... A61K 31/5585; A61K 9/0053; A61K 45/06
See application file for complete search history.

(56) References Cited

U.S. PATENT DOCUMENTS

| | | |
|---|---|---|
| 4,474,802 A | 10/1984 | Ohno et al. |
| 7,345,181 B2 | 3/2008 | Kim et al. |
| 7,776,896 B2 | 8/2010 | Guilford et al. |
| 8,183,286 B2 | 5/2012 | Faulds et al. |
| 8,779,170 B2 | 7/2014 | Sharma et al. |
| 8,980,944 B2 | 3/2015 | Faulds et al. |
| 2003/0166631 A1 | 9/2003 | Dumont et al. |
| 2003/0216474 A1 | 11/2003 | Peebles, Jr. et al. |
| 2004/0209945 A1 | 10/2004 | Szabo et al. |
| 2005/0065133 A1 | 3/2005 | Lee et al. |
| 2005/0080140 A1 | 4/2005 | Hatae et al. |
| 2007/0066618 A1 | 3/2007 | Shimojo et al. |
| 2007/0123568 A1 | 5/2007 | Jiang et al. |
| 2007/0123569 A1 | 5/2007 | Jiang et al. |
| 2010/0216689 A1 | 8/2010 | Takigawa et al. |
| 2012/0190637 A1 | 7/2012 | Guilford et al. |
| 2012/0323025 A1 | 12/2012 | Sharma et al. |
| 2013/0253218 A1 | 9/2013 | Oh et al. |
| 2014/0275237 A1 | 9/2014 | Faulds et al. |
| 2015/0196578 A1* | 7/2015 | Guilford ............ A61K 31/4166 514/43 |
| 2015/0374715 A1 | 12/2015 | Faulds et al. |
| 2018/0094244 A1 | 4/2018 | Novik et al. |
| 2018/0252727 A1 | 9/2018 | Garfall et al. |
| 2022/0168352 A1 | 6/2022 | Craigo |

FOREIGN PATENT DOCUMENTS

| | | |
|---|---|---|
| CN | 102952107 A | 3/2013 |
| DE | 102005062741 A1 | 6/2007 |
| EP | 0974580 A1 | 1/2000 |
| EP | 1563846 A1 | 8/2005 |
| EP | 1975163 A1 | 10/2008 |
| JP | H11510809 A | 9/1999 |
| JP | 2005120069 A | 5/2005 |
| JP | 2010100629 A | 5/2010 |
| KR | 101777632 B1 | 9/2017 |
| KR | 101777633 B1 | 9/2017 |
| KR | 1020170123442 A | 11/2017 |
| KR | 101821685 B1 | 1/2018 |
| WO | 1998037895 A1 | 9/1998 |
| WO | 2002090324 A1 | 11/2002 |
| WO | 2004026224 A2 | 4/2004 |
| WO | 2007057232 A1 | 5/2007 |
| WO | 2007101111 A2 | 9/2007 |
| WO | 2008058766 A1 | 5/2008 |
| WO | 2008116669 A1 | 10/2008 |
| WO | 2011047048 A1 | 4/2011 |
| WO | 2012043838 A1 | 4/2012 |
| WO | 2014151085 A1 | 9/2014 |
| WO | 2015109112 A1 | 7/2015 |
| WO | 2019/200251 A1 | 10/2019 |

OTHER PUBLICATIONS

Shen et al., Am J Respir Crit Care Med 193;2016:A7284 (Year: 2016).*
Cochrane Database Syst Rev. Sep. 2017; 2017(9): CD012783 (Year: 2017).*
Business Wire; "CytoAgents Launches Clinical Trials for GP1681, Treatment of COVID-19 Cytokine Storm", BioSpace, Oct. 13, 2020. Website article.
Huang et al., "Clinical features of patients infected with 2019 novel coronavirus in Wuhan, China," Lancet, 395 (10223): pp. 497-506 (2020).
International Search Report and Written Opinion for PCT/US2021/017751 dated Apr. 27, 2021.
Lu et al., "Genomic characterisation and epidemiology of 2019 novel coronavirus: implications for virus origins and receptor binding," Lancet, 395: pp. 565-574 (2020).

(Continued)

*Primary Examiner* — San Ming R Hui

(74) *Attorney, Agent, or Firm* — DLA PIPER LLP (US)

(57) ABSTRACT

Compositions and methods that can be used to treat or prevent a viral infection are described herein. Prostacyclin/prostaglandin analogs can be used to treat infection by viruses such as SARS-CoV, MERS-CoV, and SARS-CoV-2. For example, pharmaceutical compositions containing beraprost or salts thereof can be used to treat infection by SARS-CoV-2 (the virus that causes the "COVID-19" disease).

16 Claims, No Drawings

(56) References Cited

OTHER PUBLICATIONS

Mamula, Kris B.; "New COVID-19 treatment shows encouraging early results, North Shore biotech company says" Pittsburgh Post-Gazette, Dec. 9, 2020. Website article.

Medilink EM Patron Quotient Sciences; "Quotient Sciences and CytoAgents Accelerate Potential Treatment for COVID-19 Cytokine Storm" Apr. 28, 2020. Website article.

Midlands Innovation Health (MIH) et al.; "Mobilising Research Excellence in the Midlands to Tackle COVID-19: Showcasing the dedicated work of academics, healthcare professionals and industrial partners from across the Midlands." Article, Jan. 15, 2021, pp. 1-68.

Wang et al., "Clinical Characteristics of 138 Hospitalized Patients With 2019 Novel Coronavirus-Infected Pneumonia in Wuhan, China," JAMA, Feb. 7, 2020, vol. 323, No. 11, pp. 1061-1069; Abstract.

Akasaka et al. "Highly Sensitive Isomeric Determination of Beraprost Sodium in Plasma Using a Fluorescent Chiral Derivatization Reagent" 1997, Analytical Sciences 13:461-466.

Aldridge et al. "TNF/iNOS-Producing Dendritic Cells are the Necessary Evil of Lethal Influenza Virus Infection," Mar. 31, 2009, PNAS, 106(13):5306-5311.

Armstrong et al. "A Phase 1, Single-Center, Single-Dose, Open-Label, Randomized, Crossover, Comparative Bioavailability And Food Effect Study To Compare Bps-314d-Mr 15 µg And 60 µg Tablet Formulations To The Existing Bps-Mr 60 µg Tablet Formulation In Healthy Volunteers" 2012, American J. Respiratory and Critical Care Medicine 185:A4784 (abstract only).

Augustin et al. "The Use of Extra Corporeal Life Support in the Treatment of Influenza-Associated Myositis/Rhabdomyolysis" Mar. 1, 2006, Perfusion 21(2):121-125 (abstract only).

Clarke et al. "Identification in Human Airways Smooth Muscle Cells of the Prostanoid Receptor and Signalling Pathway Through which PGE2 Inhibits the Release of GM-CSF" Apr. 2004, British Journal of Pharmacology 141(7):1141-1150 (abstract only).

Flesch et al. "Novel Prostaglandin Receptor Modulators—part Ii: Ep Receptor Modulators; A Patent Review 2002-2012" Feb. 2013, Expert Opinion On Therapeutic Patents, 23(2):233-267, XP055118714.

Galabov et al. "Rimantadine and Oseltamivir Demonstrate Synergistic Combination Effect in an Experimental Infection with Type A (H3N2) Influenza Virus in Mice" 2006, Antiviral Chemistry Chemotherapy 17:251-258.

Honda et al. "Prostacyclin-IP Signaling and Prostaglandin E2-EP2/EP4 Signaling both Mediate Joint Inflammation in Mouse Collagen-Induced Arthritis" Feb. 20, 2006, J Exp Med. 203(2):325-335.

Hristovska et al. "Prostaglandin E2 Induces Vascular Relaxationby E-prostanoid 4 Receptor-mediated Activation of Endothelial Nitric Oxide Synthase" Sep. 2007, Hypertension 50(3):525-530.

Ohta et al. "816 Prostaglandin I2-Analogue, Beraprost Sodium, Prevents Concanavalin A-Induced Liver Injury through Improvement of Hepatic Blood Circulation and Suppression of Cytokine Production in Mice" Jan. 1, 2000, Hepatology 38(556), doi:10.1016/S0270-9139(03)80858-3, ISSN 0270-9139, XP004624031.

Reddy et al. "Formal Synthesis of Antiplatelet Drug, Beraprost" 2012, J. Organic Letters 14(1):299-301 (abstract only).

Sly et al. "Isomeric Separation of Beraprost Sodium Using an a 1-Acid Glycoprotein Column" 1993, J. Chromatography A 641:249-255 (abstract only).

Tanaka et al. "Prostaglandin E-2 Receptor Selective Agonists E-Prostanoid 2 and E-Prostanoid 4 may have Therapeutic Effects on Ovalbumin-induced Broncho constriction" Nov. 2005, Chest 128(5):3717-3723 (abstract only).

International Search Report and Written Opinion for PCT Application No. PCT/US2023/061664 dated Jul. 18, 2023.

International Search Report and Written Opinion for International Application No. PCT/US2023/067640, mailed Nov. 21, 2023.

Porter et al., "Prostaglandin E2 onhibits T cell activation-induced apoptosis and Fas-mediated cellular cytotoxicity by blockade of Fas-ligand induction", Eur. J. Immunol. 1999, 29:2360-2365.

Anonymous "Gemmus Pharma Closes $3.3M Series B Funding to Develop Superior Flu Drug" May 13, 2014, retrieved from internet: URL: https://www.inknowvation.com/sbir/sorty/gemmus-pharma-closes-33m-series-b-funding-develop-superior-flu-drug (Retrieved on Jan. 4, 2024).

European Search Report and Written Opinion for EP 21754076.4 mailed Jan. 22, 2024.

\* cited by examiner

COMPOSITIONS AND METHODS FOR TREATING CORONAVIRUS INFECTIONS

CROSS-REFERENCE TO RELATED APPLICATIONS

This application claims priority to U.S. Provisional Patent Application Ser. No. 62/975,369, which was filed on Feb. 12, 2020, entitled COMPOSITIONS AND METHODS FOR TREATING CORONAVIRUS, U.S. Provisional Patent Application Ser. No. 63/020,342, which was filed on May 5, 2020, entitled COMPOSITIONS AND METHODS FOR TREATING CORONAVIRUS INFECTIONS, and U.S. Provisional Patent Application Ser. No. 63/057,095, which was filed on Jul. 27, 2020, entitled COMPOSITIONS AND METHODS FOR TREATING CORONAVIRUS INFECTIONS, the contents of all of which are incorporated in its entirety by reference.

BACKGROUND

Coronaviruses are a large family of viruses, some causing illness in people while others do not cause disease at all. Coronaviruses usually circulate among animals, including camels, cats, and bats, but never make a cross-species jump. Recently emerged 2019-nCoV/SARS-CoV-2 is genetically distinct from both MERS-CoV and/or SARS-CoV and has proven to have a higher mortality rate which would distinguish it from other coronaviruses. Without wishing to be bound by theory, it is believed that clinical progression of the disease associated with 2019-nCoV/SARS-CoV-2 infection is different from SARS or from any other common respiratory infection previously known. It has recently been demonstrated that the newly discovered 2019—novel coronavirus (hereinafter referred to as "2019-nCoV/SARS-CoV-2"; also referred as the virus that causes the disease COVID-19) that is associated with the recent outbreaks in Wuhan, China is a potent inducer of inflammatory cytokines and chemokines, such as IL1β, IL1Rα, IL-2, IL-4, IL-6, IL-7, IL-8, IL-9, IL-10, basic FGF, GCSF, GMCSF, IFNγ, IP10, MCP1, MIP1α, MIP1β, PDGF, TNFα, and VEGF (Huang et al., Lancet, 395(10223):497-506 (2020)). Further, the cytokine and chemokine profile of the patients infected with 2019-nCoV/SARS-CoV-2 was different from that observed in the SARS coronavirus patients. For example, patients infected with 2019-nCoV/SARS-CoV-2 displayed higher levels of IL-2, IL-4, IL-7, IL-9, IL-10, basic FGF, GCSF, GM-CSF, PDGF, and VEGF in the plasma when compared to the patients infected with SARS coronavirus. Genomic sequencing revealed that 2019-nCoV/SARS-CoV-2 was only 79% identical to SARS-CoV (Lu et al., Lancet, 395: 565-574 (2020)). These studies suggest that the pathophysiology of 2019-nCoV/SARS-CoV-2 is different that of previously disclosed coronaviruses.

In 2019 an outbreak of respiratory disease caused by a novel (new) coronavirus that was first detected in China and which has now been detected in more than 100 locations internationally. The virus has been named "SARS-CoV-2" and the disease it causes has been named "coronavirus disease 2019" (abbreviated "COVID-19"). The temporary name for the virus was "2019-nCOV" until the virus was renamed SARS-CoV-2. In some literature the term "COVID-19" has also been in reference to the virus itself, to help distinguish from the virus associated with the 2003 Severe acute respiratory syndrome (SARS) disease.

Severe acute respiratory syndrome (SARS) is a viral respiratory illness caused by a coronavirus called SARS-associated coronavirus (SARS-CoV). SARS was first reported in Asia in February 2003.

Middle East Respiratory Syndrome (MERS) is an illness caused by a virus (more specifically, a coronavirus) called Middle East Respiratory Syndrome Coronavirus (MERS-CoV).

COVID-19 has a number of features that distinguish it as a disease distinct from SARS or MERS. First, the infectious period of COVID-19 is different. Peak viral shedding in SARS patients occurred after the patient were already ill with respiratory symptoms, and the patients could be easily identified. No known transmission was reported for asymptomatic or mildly symptomatic patients. In contrast, COVID-19 patients seem to transmit the disease despite being asymptomatic or having mild symptoms.

The clinical spectrum of the virus is also different. Patients with mild symptoms or who are asymptomatic are common in COVID-19. In China, 81% of the patients with confirmed COVID-19 were reported to have a mild disease or less severe forms of pneumonia, while 13.8% had a severe condition and 4.7% were critically ill. The case fatality rate (CFR) is currently estimated to be 2.3%, with increasing CFRs for patients with advanced age, compromised immunity, or comorbidities.

The community spread pattern is also different. While the SARS and MERS outbreaks were mainly propagated within hospitals, community transmission is already widespread for COVID-19. Within a few months of the first reported cases in December 2019 and January 2020, in March 2020 there have already been 120,000 reportedly infected, 4000 killed, and 114 countries reporting cases of infection.

The immune response to COVID-19 is different, COVID-19 (infection by SARS-CoV-2) initiated increased secretion of T-helper-2 (Th2) cytokines (for example, IL4 and IL10). This differs from SARS-CoV infection, which does not cause increased secretion of these cytokines.

Symptoms

The predominant symptoms of COVID-19 include fever, shortness of breath, fatigue, myalgia, and cough. Pneumonia is present in most SARS-CoV-2 infected patients. Less common symptoms include sputum production, headache, hemoptysis, and diarrhea.

The spectrum of clinical presentations of COVID-19 have ranged from asymptomatic infection to severe respiratory failure. Several symptoms associated with severity of COVID-19 disease are listed in the following Table.

| Severity of disease | Symptoms |
| --- | --- |
| Mild | Asymptomatic or mild pneumonia |
| Severe | Dyspnea, respiratory frequency ≥ 30/min, blood oxygen saturation ≤ 93%, partial pressure of arterial oxygen to fraction of inspired oxygen ratio < 300, and/or lung infiltrates > 50% within 24 to 48 hours |
| Critical | Respiratory failure, septic shock, and/or multiple organ dysfunction or failure |

Nearly half the cases had one or more coexisting medical conditions, such as hypertension, diabetes and cardiovascular disease. The case-fatality rate is elevated among those patients with coexisting medical conditions. Upon progression of the disease in severe and critical cases, the median duration period from illness onset to dyspnea was 8.0 days, and to mechanical ventilation was 10.5 days. Patients also have leucopenia and lymphopenia, and elevated lactate dehydrogenase, and creatinine kinase. Half of patients had abnormal liver function, with elevated alanine aminotransferase or aspartate aminotransferase.

Most patients showed C-reactive protein above the normal range, and one third have elevated D-dimer. Plasma CXCL-1, IL-1β, IL-1RA, IL-6, IL-7, IL-8, IL-9, IL-10, basic FGF, GCSF, GMCSF, IFNγ, IP10, MCP1, MIP1α, MIP1β, PDGF, TNFα, and VEGF concentrations were higher in patients than in healthy adults. Further comparisons between patients needing intensive care unit (ICU) and non-ICU patients showed that plasma concentrations of IL2, IL7, IL10, GCSF, IP10, MCP1, MIP1α, and TNFα were higher in ICU patients than non-ICU patients.

Radiologic findings of chest computed tomography (CT) indicate that two thirds of patients had at least two affected lobes (of the lung), while nearly half of patients had five affected lobes. The most common manifestations are patchy ground glass opacities (GGO) and patchy consolidation, distribution mainly in the middle and outer zone of the lung.

An analysis of 819 confirmed COVID-19 adult patients in Wuhan, China revealed an association of older age, higher Sequential Organ Failure Assessment (SOFA) score, and elevated d-Dimer at admission as risk factors for mortality. Many patients had other medical comorbidities. Common complications include sepsis, respiratory failure, ARDS, heart failure, septic shock, coagulopathy, acute cardiac injury, acute kidney injury, secondary infection, hypoproteinaemia, and acidosis. Common comorbidities that were present include hypertension, diabetes, and coronary artery disease.

Mechanisms of Infection

The envelope spike (S) protein mediates receptor binding and membrane fusion and is crucial for determining host tropism and transmission capacity. Broadly speaking, the S protein is functionally divided into the S1 domain, responsible for receptor binding, and S2 domain, responsible for cell membrane fusion. SARS-CoV-2 is believed to use the Angiotensin converting enzyme II (ACE2) cell receptor for cell entry.

It has been reported that S protein of SARS-CoV-2 binds ACE2 with approximately 10- to 20-fold higher affinity than the S protein of SARS-CoV. The high affinity of S protein for human ACE2 may facilitate the spread of SARS-CoV-2 in humans. In contrast, SARS-CoV-2 does not use receptors used by other coronaviruses to enter cells, such as aminopeptidase N and dipeptidyl peptidase 4 (DPP4).

ACE2 is highly expressed in renal tubular cells, Leydig cells and cells in seminiferous ducts in testis. Therefore, SARS-CoV-2 might show an increased binding to these ACE2 positive cells and damage the kidney and testicular tissue of patients.

"Cytokine Storm" with COVID-19

Respiratory failure from acute respiratory distress syndrome (ARDS) is the leading cause of mortality in COVID-19 patients and a subgroup of patients with severe (and critical) COVID-19 might have a cytokine storm syndrome. Secondary haemophagocytic lymphohistiocytosis (sHLH) is a hyperinflammatory syndrome characterized by a severe and sudden onset of and hypercytokinaemia with multiorgan failure and eventual fatality. A cytokine profile resembling sHLH is associated with COVID-19 disease severity, characterized by elevated levels of IL-2, IL-7, GCSF, IFN-γ, IP-10, MCP1, MIP1-α, and TNFα.

Predictors of fatality from a recent retrospective, multicentre study of 150 confirmed COVID-19 cases in Wuhan, China, included elevated ferritin and IL-6 suggesting that mortality might be due to SARS-CoV-2 driven hyperinflammation.

Sex-Specific Differences

Interestingly, there are no sex-specific differences in initially contracting the COVID-19 disease, but there are statistically meaningful sex-specific differences in subsequent disease progression. An analysis of patients with confirmed COVID-19 disease in China revealed a male to female ratio of 0.99:1 in Wuhan, 1.04:1 in Hubei, and 1.06:1 in the country as a whole. Sex-specific differences in refractory vs non-refractory COVID-19 were clear, however. An analysis of refractory vs non-refractory COVID-19 cases revealed that refractory cases were more likely to be male. In fact, the odds ratio was 2.206, indicating that patients with refractory cases of COVID-19 were more likely to be male. Refractory patients were also more likely to have more comorbidities. The odds ratio is the "measure of association" for a case-control study. It quantifies the relationship between an exposure (such as eating a food or attending an event) and a disease in a case-control study. The odds ratio is calculated using the number of case-patients who did or did not have exposure to a factor (such as a particular food) and the number of controls who did or did not have the exposure. The odds ratio indicates how much higher the odds of exposure are among case-patients than among controls. An odds ratio of 1.0 (or close to 1.0) indicates that the odds of exposure among case-patients are the same as, or similar to, the odds of exposure among controls. The exposure is not associated with the disease. Greater than 1.0 indicates that the odds of exposure among case-patients are greater than the odds of exposure among controls. The exposure might be a risk factor for the disease. Less than 1.0 indicates that the odds of exposure among case-patients are lower than the odds of exposure among controls. The exposure might be a protective factor against the disease.

A Strong Need Exists for Effective Treatments

COVID-19 represents a challenging and unique disease to be battled. There are currently no commercially available effective treatments. There exists a need for new and improved treatments and compositions for treating and/or preventing SARS-CoV-2 infection and the resulting COVID-19 disease.

SUMMARY

Disclosed herein are methods and compositions to treat viral infections. Examples of viral infections include SARS-CoV, MERS-CoV, and SARS-CoV-2.

Methods can generally comprise administering a pharmaceutical composition to a subject. The pharmaceutical composition can comprise an effective amount of a prostacyclin/prostaglandin analog, such as analogs selected from the group consisting of carbaprostacyclin, beraprost, taprostene, nileprost, iloprost, cicaprost, ciprostene, treprostinil, bonsentan, uoprost, eptaloprost, or an isomer thereof, and pharmaceutically acceptable salts thereof. In some embodiments, the prostacyclin/prostaglandin analog is beraprost or a beraprost salt. The salt can be a pharmaceutically acceptable salt of beraprost. The beraprost can be a beraprost isomer, such as beraprost GP1681.

In an embodiment, a method of treating 2019-nCoV infection in a subject comprises administering to subject in need thereof a pharmaceutical composition comprising an effective amount of a prostacyclin/prostaglandin analog. In some embodiments, the prostacyclin/prostaglandin analog is beraprost, a beraprost salt, or an isomer of beraprost GP1681. In some embodiments, the method further comprises administering an additional agent selected from the group consisting of oseltamivir (Tamiflu™), zanamivir (Relenza™) amantadine, rimantadine, remdesivir, chloroquine, ritonavir, lopinavir, ribavirin, penciclovir, nitazoxanide, nafamostat, favipiravir, corticosteroids, and combinations thereof.

In an embodiment, a method of reducing the pro-inflammatory cytokines and chemokines in the subject's lung following 2019-nCoV infection comprises administering to subject in need thereof a pharmaceutical composition comprising an effective amount of a prostacyclin/prostaglandin analog. In some embodiments, the prostacyclin/prostaglandin analog is beraprost or an isomer of beraprost GP1681. In some embodiments, the method further comprises administering an additional agent selected from the group consisting of oseltamivir (Tamiflu™), zanamivir (Relenza™), amantadine, rimantadine, remdesivir, chloroquine, ritonavir, lopinavir, ribavirin, penciclovir, nitazoxanide, nafamostat, favipiravir, corticosteroids, and combinations thereof. In some embodiments, pro-inflammatory cytokines are selected from IL-1α, IL-β, IL-2, IL-4, IL-6, IL-7, IL-8, IL-10, IL-12, INF-α, INF-γ, TNF-α, IP-10, MCP-1, MIP-1, RANTES, and combinations thereof.

In an embodiment, a method of treating a severe respiratory illness due to 2019-nCoV infection and characterized by upregulation of IL-2, IL-4, IL-6, IL-7, IL-8, and IL-10 comprises administering to subject in need thereof a pharmaceutical composition comprising an effective amount of a prostacyclin/prostaglandin analog. In some embodiments, the prostacyclin/prostaglandin analog is beraprost or an isomer of beraprost GP1681. In some embodiments, the method further comprises administering an additional agent selected from the group consisting of oseltamivir (Tamiflu™), zanamivir (Relenza™), amantadine, rimantadine, remdesivir, chloroquine, ritonavir, lopinavir, ribavirin, penciclovir, nitazoxanide, nafamostat, favipiravir, corticosteroids, and combinations thereof.

In an embodiment, a method of downregulating the levels of cytokines selected from IL-2, IL-4, IL-6, IL-7, IL-8, and IL-10 that are associated with 2019-nCoV infection, the method comprises administering to a subject in need thereof a pharmaceutical composition comprising an effective amount of a prostacyclin/prostaglandin analog. In some embodiments, the prostacyclin/prostaglandin analog is beraprost or an isomer of beraprost GP1681. In some embodiments, the method further comprises administering an additional agent selected from the group consisting of oseltamivir (Tamiflu™), zanamivir (Relenza™) amantadine, rimantadine, remdesivir, chloroquine, ritonavir, lopinavir, ribavirin, penciclovir, nitazoxanide, nafamostat, favipiravir, corticosteroids and combinations thereof.

Definitions

As used herein, the term "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation.

As used herein the term "analog" refers to a compound, the presence of which results in a biological activity of a receptor that is the same as the biological activity resulting from the presence of a naturally occurring ligand for the receptor.

The terms "administer," "administering" or "administration" as used herein refer to directly administering a compound or a composition to a subject.

As used herein, the term "effective amount" refers to an amount that results in measurable inhibition of at least one symptom or parameter of a specific disorder or pathological process. As used herein the term "therapeutically effective amount" of compositions of the application is an amount, which confers a therapeutic effect on the treated subject, at a reasonable benefit/risk ratio applicable to any medical treatment. The therapeutic effect may be objective (that is, measurable by some test or marker) or subjective (that is, subject gives an indication of or feels an effect or physician observes a change).

As used herein the term "immediate release" refers to pharmaceutical compositions that release the active ingredient within a short period of time.

As used herein the term "modified release" refers to pharmaceutical compositions that does not otherwise release the active ingredient immediately, for example it may release the active ingredient at a sustained or controlled rate over an extended period of time, or may release the active ingredient after a lag time after administration, or may be used optionally in combination with an immediate release composition. Modified release includes extended release, sustained release, and delayed release. The term "extended release" or "sustained release" as used herein is a dosage form that makes a drug available over an extended period of time after administration. The term "delayed release" as used herein is a dosage form that releases a drug at a time other than immediately upon administration.

The phrase "pharmaceutically acceptable salt(s)", as used herein, includes those salts of compounds of the application that are safe and effective for use in mammals and that possess the desired biological activity. Pharmaceutically acceptable salts include salts of acidic or basic groups present in compounds of the application or in compounds identified pursuant to the methods of the application. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the application can form pharmaceutically acceptable salts with various amino acids. Suitable base salts include, but are not limited to, aluminum, calcium, lithium, magnesium, potassium, sodium, zinc, iron and diethanolamine salts. Pharmaceutically acceptable base addition salts are also formed with amines, such as organic amines. Examples of suitable amines are N,N'-dibenzylethylenediamine, chloroprocaine, choline, diethanolamine, dicyclohexylamine, ethylenediamine, N-methylglucamine, and procaine.

The term "preventing" may be taken to mean to prevent a specific disorder, disease or condition and/or prevent the reoccurrence of a specific disorder, disease or condition.

The term "substantially pure isomer" refers to a formulation or composition wherein among various isomers of a compound a single isomer is present at 70%, or greater or at 80% or greater, or at 90% or greater, or at 95% or greater, or at 98% or greater, or at 99% or greater, or said compound or composition comprise only a single isomer of the compound.

As used herein the terms "treat", "treated", or "treating" refer to both therapeutic treatment and prophylactic or preventative measures, wherein the object is to protect against (partially or wholly) or slow down (for example, lessen or postpone the onset of) an undesired physiological condition, disorder or disease, or to obtain beneficial or desired clinical results such as partial or total restoration or inhibition in decline of a parameter, value, function or result that had or would become abnormal. For the purposes of this application, beneficial or desired clinical results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease. Treatment seeks to elicit a clinically significant response without excessive levels of side effects.

The term "unit dosage form" refers to physically discrete units suitable as a unitary dosage for human subjects and other animals, each unit containing a predetermined quantity of active material calculated to produce the desired therapeutic effect, in association with a suitable pharmaceutical excipient.

The "weight percent" disclosed herein may be weight-to-weight percent or weight-to-volume percent, depending upon the composition.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a medical condition or disorder. Such administration encompasses co-administration of these therapeutic agents in a substantially simultaneous manner, such as in a single capsule, or dosage presentation, having a fixed ratio of active ingredients or in multiple, separate capsules for each active ingredient. In addition, such administration also encompasses use of each type of therapeutic agent in a sequential manner in the same patient, with delivery of the individual therapeutics separated by 1-24 hours, 1-7 days, or 1 or more weeks. In either case, the treatment regimen will provide beneficial effects of the drug combination in treating the conditions or disorders described herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

DETAILED DESCRIPTION

This disclosure is not limited to the particular systems, devices and methods described, as these may vary. The terminology used in the description is for the purpose of describing the particular versions or embodiments only, and is not intended to limit the scope.

Various methods and kits are described herein for the treatment of viral infection in a subject. The methods can include administration of at least one pharmaceutical composition to the subject. Treatment may be effective against one or more symptoms of the viral infection. The treatment can reduce or eliminate harmful effects of the viral infection. The viral infection can be a coronavirus infection, a SARS-CoV infection, a MERS-CoV infection, or a SARS-CoV-2 infection. In some examples, the viral infection can be a SARS-CoV-2 infection.

Increased production of cytokines triggers inflammation, a normal response by the body to help fight a virus. However, when cytokine production becomes prolonged or excessive it can inflame airways, making it hard to breathe, which in turn can result in pneumonia and acute respiratory distress; and it can injure other organs, which can result in severe life-threatening complications.

Prostacyclins and prostaglandins exert their effects through their G protein-coupled receptors (GPCR) which are located on the cell surface. Many of the prostacyclin and prostaglandin receptors have been cloned and characterized. In the case of Prostaglandin I2 (PGI2) and Prostaglandin E2 (PGE2), a wide variety of cellular effects result from binding to the Prostaglandin I2 receptor (IP) or the Prostaglandin EP4 receptor (PGE2). While not wishing to be bound by theory, Applicant currently believes that the prostacyclin/prostaglandin analogs inhibit the release of pro-inflammatory cytokines and chemokines by acting through cAMP and NF-kB pathways to downregulate downstream cytokine production. This inhibition allows suppression of the inflammatory response to the viral infection. The inflammation is reduced while preserving immune response so immunity is maintained.

Pharmaceutical Compositions

The pharmaceutical composition can comprise at least one prostacyclin/prostaglandin analog. Examples of prostacyclin or prostaglandin analogs include carbaprostacyclin, beraprost, taprostene, nileprost, iloprost, cicaprost, ciprostene, treprostinil, bonsentan, uoprost, eptaloprost, or an isomer thereof, and pharmaceutically acceptable salts thereof. In some embodiments, the pharmaceutical composition comprises an effective amount of beraprost or a pharmaceutically acceptable salt thereof. Beraprost has a chemical formula $C_{24}H_{30}O_5$ and has a single carboxylic acid group. In some embodiments, the prostacyclin analog is a beraprost salt such as beraprost sodium ($C_{24}H_{29}NaO_5$; 2,3,3a,8b-tetrahydro-2-hydroxyl-1-(3-hydroxyl-4-methyl-1-octen-6-ynyl)-1H-cyclopenta[b]benzofuran-5-butanoic acid, sodium salt). Beraprost sodium (BPS) is a mixture of four isomers—two diastereomers (BPS-314 and BPS-315) and their two enantiomers each which are BPS-314d (GP1681; also called esuberaprost) and BPS-3141 (GP1684), and BPS-315d (GP1683) and BPS-3151 (GP1682). Beraprost isomers are further described in U.S. Patent Publication No. US 2014-0275237 A1. In some examples, the pharmaceutical composition can contain 1, 2, 3, or all 4 isomers of beraprost. In some embodiments, the beraprost isomer is BPS-314d (GP1681; esuberaprost sodium salt).

Beraprost and methods for its preparation are shown in U.S. Pat. No. 7,345,181 and PCT Publication No. WO 2004/026224, entitled "Process for preparing prostaglandin derivatives and starting materials for the same". Beraprost is commercially available from Yonsung Fine Chemicals (Gyeonggi-do, Republic of Korea). The beraprost can be present in the pharmaceutical composition at generally any effective amount or effective concentration. Different pharmaceutical forms may have different amounts or concentrations of beraprost.

In some embodiments, the effective amount of beraprost or an isomer thereof or a pharmaceutically acceptable salt thereof are present in a unit dose of the pharmaceutical composition is at least about 1 microgram, about 1 microgram to about 100 micrograms, about 1 microgram to about 80 micrograms, about 1 microgram to about 60 micrograms, about 1 microgram to about 50 micrograms, about 1 microgram to about 40 micrograms, about 51 microgram to about 30 micrograms, about 1 microgram to about 20 micrograms, about 1 mg to about 10 micrograms, or about 1 microgram to about 5 micrograms, or any value between these ranges. Specific examples include about 1 microgram, about 5 micrograms, about 10 micrograms, about 25 micrograms, about 50 micrograms, about 75 micrograms, about 100 micrograms, or ranges between any two of these values.

Additional specific examples include about 10 micrograms, about 15 micrograms, and about 20 micrograms. Further specific examples include about 30 micrograms, about 45 micrograms, about 60 micrograms, and about 45 micrograms to about 60 micrograms. For example, about 15 micrograms to about 20 micrograms can be administered three times a day (TID) for a total daily dosage of about 45 micrograms to about 60 micrograms. In some examples, the dosage can be changed over time. For example, an initial dosage of about 15 micrograms three times a day (TID) for a first period of time, followed by an increased dosage of about 20 micrograms three times a day (TID) for a second period of time.

In some embodiments, the amount of beraprost or an isomer thereof or a pharmaceutically acceptable salt thereof can be calculated based on the presence of a single desired isomer. For example, if a single isomer, such as BPS-314d (GP1681; esuberaprost sodium salt) is desired at an amount of about 15 micrograms to about 90 micrograms, this is equivalent to an amount of about 60 micrograms to about 360 micrograms of a racemic mixture of four isomers (where the amount of a single isomer is one-quarter of the mass).

In some embodiments, the pharmaceutical composition comprising beraprost or an isomer thereof or a pharmaceutically acceptable salt thereof achieves a Cmax of about 0.01 nanomolar to about 10 nanomolar, about 0.01 nanomolar to about 5 nanomolar, about 0.01 nanomolar to about 3 nanomolar, about 0.01 nanomolar to about 2 nanomolar, about 0.01 nanomolar to about 1 nanomolar, about 0.01 nanomolar to about 0.5 nanomolar, or any values between these ranges. Specific examples include about 0.01 nanomolar, about 0.05 nanomolar, about 0.075 nanomolar, about 0.1 nanomolar, about 0.5 nanomolar, about 1 nanomolar, about 2 nanomolar, about 5 nanomolar, or about 10 nanomolar.

In some embodiments, the pharmaceutical composition comprising beraprost or an isomer thereof or a pharmaceutically acceptable salt thereof achieves a Tmax at about 0.1 hour to about 5 hours, about 0.1 hour to about 4 hours, about 0.1 hour to about 3 hours, about 0.1 hour to about 2 hours, about 0.1 hour to about 1 hours, or any specific value between these ranges. Specific examples include about 0.1 hour, about 0.5 hour, about 1 hour, about 1.5 hours, about 1.7 hours, about 2 hours, or about 5 hours.

In some embodiments, the pharmaceutical composition comprising beraprost or an isomer thereof or a pharmaceutically acceptable salt thereof achieves an AUC of about 0.01 ng·hr/mL to about 30 ng·hr/mL over a 48 hour period, about 0.01 ng·hr/mL to about 20 ng·hr/mL over a 48 hour period, about 0.01 ng·hr/mL to about 10 ng·hr/mL over a 48 hour period, about 0.01 ng·hr/mL to about 5 ng·hr/mL over a 48 hour period, about 0.01 ng·hr/mL to about 3 ng·hr/mL over a 48 hour period, about 0.01 ng·hr/mL to about 2 ng·hr/mL over a 48 hour period, or about 0.01 ng·hr/mL to about 1 ng·hr/mL over a 48 hour period. Specific examples include about 0.01 ng·hr/mL, about 0.05 ng·hr/mL, about 0.1 ng·hr/mL, about 0.5 ng·hr/mL, about 1 ng·hr/mL, about 2 ng·hr/mL, about 5 ng·hr/mL, about 10 ng·hr/mL, or about 30 ng·hr/mL.

In some examples, the pharmaceutical composition can further comprise at least one antiviral component. This can be part of a combination therapy approach. Examples of antiviral components include oseltamivir (Tamiflu™), zanamivir (Relenza™), baloxavir marboxil (Xofluza™), amantadine, rimantadine, remdesivir, chloroquine, ritonavir, lopinavir, ribavirin, penciclovir, nitazoxanide, nafamostat, favipiravir, and combinations thereof. In some examples, the pharmaceutical composition can further comprise at least one anti-inflammatory component such as a corticosteroid.

In some examples, the pharmaceutical composition further comprises one or more pharmaceutically acceptable excipients. Examples of pharmaceutically acceptable excipients that may be present in the composition include but not limited to fillers/vehicles, solvents/co-solvents, preservatives, antioxidants, suspending agents, surfactants, antifoaming agents, buffering agents, chelating agents, sweeteners, flavoring agents, binders, extenders, disintegrants, diluents, lubricants, fillers, wetting agents, glidants, and combinations thereof.

In some examples, the pharmaceutic composition can further comprise one or more exemplary fillers. Examples of exemplary fillers include cellulose and cellulose derivatives such as microcrystalline cellulose; starches such as dry starch, hydrolyzed starch, and starch derivatives such as corn starch; cyclodextrin; sugars such as powdered sugar and sugar alcohols such as lactose, mannitol, sucrose and sorbitol; inorganic fillers such as aluminum hydroxide gel, precipitated calcium carbonate, carbonate, magnesium aluminometasilicate, dibasic calcium phosphate; and sodium chloride, silicon dioxide, titanium dioxide, titanium oxide, dicalcium phosphate dihydrate, calcium sulfate, alumina, kaolin, talc, or combinations thereof. Fillers may be present in the composition from about 20 wt % to about 65 wt %, about 20 wt % to about 50 wt %, about 20 wt % to about 40 wt %, about 45 wt % to about 65 wt %, about 50 wt % to about 65 wt %, or about 55 wt % to about 65 wt % of the total weight of the composition, or any value between these ranges.

In some examples, the pharmaceutical composition further comprises one or more disintegrants. Examples of disintegrants include starches, alginic acid, crosslinked polymers such as crosslinked polyvinylpyrrolidone, croscarmellose sodium, potassium starch glycolate, sodium starch glycolate, clays, celluloses, starches, gums, or combinations thereof. Disintegrants may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some examples, the pharmaceutical composition further comprises one or more binders, including but not limited to celluloses such as hydroxypropylcellulose, methyl cellulose, and hydroxypropylmethylcellulose; starches such as corn starch, pregelatinized starch, and hydroxypropyl starch; waxes and natural and synthetic gums such as acacia, tragacanth, sodium alginate; synthetic polymers such as polymethacrylates and polyvinylpyrrolidone; and povidone, dextrin, pullulane, agar, gelatin, tragacanth, macrogol, or combinations thereof. Binders may be present in the composition from about 0.5 wt % to about 5 wt %, about 0.5 wt % to about 4 wt %, about 0.5 wt % to about 3 wt %, about 0.5 wt % to about 2 wt %, or about 0.5 wt % to about 1 wt % of the total weight of the composition, or any value between these ranges.

In some examples, the pharmaceutical composition further comprises one or more wetting agents, including but not limited to oleic acid, glyceryl monostearate, sorbitan monooleate, sorbitan monolaurate, triethanolamine oleate, polyoxyethylene sorbitan mono-oleate, polyoxyethylene sorbitan monolaurate, sodium oleate, sodium lauryl sulfate, poloxamers, poloxamer 188, polyoxyethylene ethers, polyoxyethylene sorbitan fatty acid esters, polyoxyethylene fatty acid esters, polyethylene glycol fatty acid esters, polyoxyethylene hardened castor oil, polyoxyethylene alkyl ethers, polysorbates, cetyl alcohol, glycerol fatty acid esters (e.g., triacetin, glycerol monostearate, etc.), polyoxymethylene stearate, sodium lauryl sulfate, sorbitan fatty acid esters, sucrose fatty acid esters, benzalkonium chloride, polyethoxylated castor oil, and combinations thereof. Wetting agents may be present in the composition from about 0.1 wt % to about 1 wt %, about 0.1 wt % to about 2 wt %, about 0.1 wt % to about 3 wt %, about 0.1 wt % to about 4 wt %, or about 0.1 wt % to about 5 wt % of the total weight of the composition, or any value between these ranges.

In some examples, the pharmaceutical composition further comprises one or more lubricants, including but not limited to stearic acid, magnesium stearate, calcium hydroxide, talc, corn starch, sodium stearyl fumarate, alkali-metal and alkaline earth metal salts, waxes, boric acid, sodium benzoate, sodium acetate, sodium chloride, leucine, polyethylene glycol (PEG), a methoxypolyethylene glycol, propylene glycol, sodium oleate, glyceryl behenate, glyceryl palmitostearate, glyceryl benzoate, magnesium lauryl sulfate, sodium lauryl sulfate, and combinations thereof. Lubricants may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

In some examples, the pharmaceutical composition further comprises one or more glidants, including but not limited to colloidal silicon dioxide, talc, sodium lauryl sulfate, native starch, and combinations thereof. Glidants may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some examples, the pharmaceutical composition is a tablet and further comprises a top coat, such as hydroxypropyl-methylcellulose coating or polyvinyl alcohol coating, and are available under the trade name Opadry, such as Opadry White, Opadry II (Opadry is a registered trademark of BPSI Holdings LLC, Wilmington, DE, USA). Top coats may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some examples, the pharmaceutical composition can further comprise one or more preservative agents. Examples of preservative agents include sodium benzoate, paraoxybenzoic acid esters, methyl, ethyl, butyl, and propyl parabens, chlorobutanol, benzyl alcohol, phenylethylalcohol, dehydroacetic acid, sorbic acid, benzalkonium chloride (BKC), benzethonium chloride, phenol, phenylmercuric nitrate, thimerosal, or combinations thereof. Preservative agents can be included in the liquid dosage form. The preservative agents can be in an amount sufficient to extend the shelf-life or storage stability, or both, of the liquid dosage form. Preservatives may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some examples, the pharmaceutical composition can further comprise one or more flavoring agents. Examples of flavoring agents include synthetic flavor oils and flavoring aromatics and/or natural oils, extracts from plants leaves, flowers, fruits, and so forth and the like or any combinations thereof. Additional examples include cinnamon oil, oil of wintergreen, peppermint oils, clove oil, bay oil, anise oil, *eucalyptus*, thyme oil, cedar leaf oil, oil of nutmeg, oil of sage, oil of bitter almonds, and *cassia* oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, strawberry flavor, tutti-fruity flavor, mint flavor, or any combinations thereof. Flavoring agents may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

In some examples, the pharmaceutical composition can further comprise one or more antioxidants. Examples of antioxidants include flavonoids, anthocyanidins, anthocyanins, proanthocyanidins, or combinations thereof. Antioxidants may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

Physical Form of the Pharmaceutical Composition

The pharmaceutical compositions can generally be in any physical form suitable for use in treating a subject. These forms can be referred to as a unit dosage form, such as an individual pill or tablet. In some examples, the pharmaceutical compositions can be formulated as tablets, capsules, granules, powders, liquids, suspensions, gels, syrups, slurries, suppositories, patches, nasal sprays, aerosols, injectables, implantable sustained-release formulations, or mucoadherent films. In some examples, the pharmaceutical composition may be formed as a tablet, a bi-layer tablet, a capsule, a multiparticulate, a drug coated sphere, a matrix tablet, or a multicore tablet. A physical form can be selected according to the desired method of treatment. In some examples, the physical form can be a liquid, for example for oral or IV, IP, IM, or IT administration.

Pharmaceutical compositions can be manufactured by various conventional methods such as conventional mixing, dissolving, granulating, dragee-making, levigating, emulsifying, encapsulating, entrapping, or lyophilizing processes. Pharmaceutical compositions can be formulated in a conventional manner using one or more physiologically acceptable carriers, diluents, excipients or auxiliaries that facilitate processing of the active agent into preparations that can be used pharmaceutically. Proper formulation can be selected upon the route of administration chosen.

For topical administration the pharmaceutical compositions described herein may be formulated as solutions, gels, ointments, creams, suspensions, and the like as are well-known in the art. Systemic compositions include, but are not limited to, those designed for administration by injection, for example, subcutaneous, intravenous injection (IV), intramuscular injection (IM), intrathecal injection (IT), intraperitoneal injection (IP), as well as those designed for transdermal, subcutaneous, transmucosal oral, or pulmonary administration. For injection, the pharmaceutical compositions can be formulated in aqueous solutions, preferably in physiologically compatible buffers such as Hanks solution, Ringer's solution, or physiological saline buffer and/or in certain emulsion formulations. The solution can contain one or more formulatory agents such as suspending, stabilizing and/or dispersing agents. In certain examples the pharmaceutical compositions can be provided in powder form for constitution with a suitable vehicle, for example, sterile pyrogen-free water, before use. For transmucosal administration, one or more penetrants appropriate to the barrier to be permeated can be used in the formulation. Such penetrants are generally known in the art.

For oral administration, the pharmaceutical compositions can combine the beraprost with one or more pharmaceutically acceptable carriers well known in the art. Such carriers facilitate formulation as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

For administration by inhalation, the pharmaceutical compositions can be delivered in the form of an aerosol spray from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

In some examples, the pharmaceutical compositions are immediate release pharmaceutical compositions, modified release pharmaceutical compositions, or a combination thereof. In some examples, the immediate release pharmaceutical composition releases the beraprost within a short period of time after administration, typically less than about 4 hours, less than about 3.5 hours, less than about 3 hours, less than about 2.5 hours, less than about 2 hours, less than about 90 minutes, less than about 60 minutes, less than about 45 minutes, less than about 30 minutes, less than about 20 minutes, or less than about 10 minutes.

In some examples, the modified release composition may release the beraprost at a sustained or controlled rate over an extended period of time, or may release it after a lag time after administration. For example, it may be released from the composition 4 hours after administration, 8 hours after administration, 12 hours after administration, 16 hours after administration, or 24 hours after administration. Modified release compositions include extended release, sustained release and delayed release compositions. In some examples, the modified release compositions may release about 10% in about 2 hours, about 20% in 2 hours, about 40% in about 2 hours, about 50% in about 2 hours, about 10% in about 3 hours, about 20% in 3 hours, about 40% in about 3 hours, about 50% in about 3 hours, about 10% in about 4 hours, about 20% in 4 hours, about 40% in about 4 hours, about 50% in about 4 hours, about 10% in about 6 hours, about 20% in 6 hours, about 40% in about 6 hours, or about 50% in about 6 hours.

In some examples, modified release compositions may comprise a matrix selected from microcrystalline cellulose, sodium carboxymethylcellulose, hydroxyalkylcelluloses such as hydroxy propyl methylcellulose and hydroxypropylcellulose, polyethylene oxide, alkylcelluloses such as methylcellulose and ethylcellulose, polyethylene glycol, polyvinylpyrrolidone, cellulose acetate, cellulose acetate butyrate, cellulose acetate phthalate, cellulose acetate trimellitate, polyvinyl acetate phthalate, polyalkylmethacrylates, polyvinyl acetate and mixtures thereof.

The modified release compositions can also be formulated as a depot preparation. Such long-acting formulations can be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Methods of Treatment

The compounds and pharmaceutical compositions described herein may be administered at therapeutically effective dosage levels to treat the recited conditions, disorders, and diseases.

The compounds and pharmaceutical compositions described herein may be administered at prophylactically effective dosage levels to mitigate or prevent the recited conditions, disorders, and diseases.

Administration may be performed by generally any method. Example delivery methods of administering include topical delivery, subcutaneous delivery, intravenous injection (IV) delivery, intramuscular injection (IM) delivery, intrathecal injection (IT) delivery, intraperitoneal injection (IP) delivery, transdermal delivery, subcutaneous delivery, oral delivery, transmucosal oral delivery, pulmonary delivery, inhalation delivery, intranasal delivery, buccal delivery, rectal delivery, vaginal delivery, and combinations thereof. In some examples, the administering comprises oral delivery.

The daily dose of prostacyclin/prostaglandin analog or beraprost or pharmaceutically acceptable salt thereof can generally be any effective amount or dosage. For example, the therapeutically effective amount (in micrograms) may include about 0.1 µg to about 100 µg, about 10 µg to about 90 µg, or about 15 µg to about 90 µg. The mass values are the combined salt weight, that is the anion and cation together. Specific examples of therapeutically effective amounts include about 0.1 µg, about 1 µg, about 10 µg, about 20 µg, about 30 µg, about g, about 50 µg, about 60 µg, about 70 µg, about 80 µg, about 90 µg, about 100 µg, and ranges between any two of these values. When administered in two or more daily doses, the amount in each dose can be added together to yield a total daily dose. For example, GP1681 may be administered at a dose of about 15-90 µg/day divided into 3 doses, and each individual dose of about 5-30 ag. Specific examples of total daily dose include about 15 ag, about 30 ag, about 45 ag, about 60 ag, and ranges between any two of these values such as about 45 ag to about 60 µg.

Use of the described methods and pharmaceutical compositions can result in a reduction or elimination of disease, symptom, virus concentration, or other undesired property in a subject relative to a control population (for example, same or similar viral infection but without treatment by the described methods and materials). The reduction can generally be reduced by any amount. For example, the reduction can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, and in an ideal situation, about 100% reduction (complete elimination of disease, symptom, virus concentration, or other undesired property).

In some examples, the methods disclosed herein to treat viral or SARS-CoV-2 infection may have the following primary outcome measures: Time to Clinical Improvement (TTCI) [Censored at Day 28] [Time Frame: up to 28 days] TTCI is defined as the time (in days) from initiation of study treatment (active or placebo) until a decline of two categories from admission status on a six-category ordinal scale of clinical status which ranges from 1 (discharged) to 6 (death). The six-category ordinal scale are—6. Death; 5. ICU, requiring ECMO and/or IMV (invasive mechanical ventilation); 4. WCU/hospitalization, requiring NIV (non-invasive mechanical ventilation)/HFNC (high-flow nasal cannula therapy); 3. Hospitalization, requiring supplemental oxygen (but not NIV/HFNC); 2. Hospitalization, not requiring supplemental oxygen; and 1. Hospital discharge.

In some examples, the methods disclosed herein to treat viral or SARS-CoV-2 infection may have the following secondary outcome measures:

| Secondary outcome | Measurement |
|---|---|
| 1 | Clinical status [Time Frame: days 7, 14, 21, and 28]. Clinical status, assessed by the ordinal scale at fixed time points (days 7, 14, 21, and 28). |
| 2 | Time to Hospital Discharge OR NEWS2 (National Early Warning Score 2) of ≤2 maintained for 24 hours. [Time Frame: up to 28 days]. Time to Hospital Discharge OR NEWS2 (National Early Warning Score 2) of ≤2 maintained for 24 hours. |
| 3 | All cause mortality [Time Frame: up to 28 days] |
| 4 | Duration (days) of mechanical ventilation [Time Frame: up to 28 days] |
| 5 | Duration (days) of extracorporeal membrane oxygenation [Time Frame: up to 28 days] |
| 6 | Duration (days) of supplemental oxygenation [Time Frame: up to 28 days] |
| 7 | Length of hospital stay (days) [Time Frame: up to 28 days] |
| 8 | Time to SARS-COV-2 RT-PCR negativity in upper and lower respiratory tract specimens [Time Frame: up to 28 days] |
| 9 | Change (reduction) in SARS-COV-2 viral load in upper and lower respiratory tract specimens as assessed by area under viral load curve. [Time Frame: up to 28 days] |
| 10 | Frequency of serious adverse drug events [Time Frame: up to 28 days] |

The treatments can generally be performed at any effective schedule. For example, the pharmaceutical compositions disclosed herein may be administered once, as needed, once daily (qd or QD), twice daily (bid or BD), three times a day (tid or TD), four times a day (qid or QID), once a week, twice a week, three times a week, four times a week, five times a week, six times a week, seven times a week, every other week, every other day, or the like for one or more dosing cycles. Alternatively, the administration can be performed based on number of hours such as every 8 hours (q8H), every 12 hours (Q12H), or every 24 hours (q24H). A dosing cycle may include administration for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, or longer. After this cycle, a subsequent cycle may begin approximately 1, 2, 3, 4, 5, 6, 7, 8, 9, 10, 11, or 12 weeks later. The treatment regime may include 1, 2, 3, 4, 5, or 6 cycles, each cycle being spaced apart by approximately 1, 2, 3, 4, 5, 6, 7, 8, 9, 10, 11, or 12 weeks. It will be understood that the specific dose level and frequency of dosage for any particular subject can be varied and will depend upon a variety of factors including the species, age, body weight, general health, gender and diet of the subject, the mode and time of administration, rate of excretion, drug combination, and severity of the particular condition.

Methods of Inhibiting Release of Cytokines and/or Chemokines

In some examples, the pharmaceutical composition inhibits the release of pro-inflammatory cytokines and/or chemokines in human alveolar and bronchial epithelial cells. In some examples, the pharmaceutical composition inhibits the release of pro-inflammatory cytokines and/or chemokines in human pulmonary endothelial cells. In some examples, the pharmaceutical composition inhibits the release of inflammatory cytokines and/or chemokines in peripheral blood mononuclear cells including lymphocytes, monocytes, macrophage, and dendritic cells.

For example, a method of reducing the pro-inflammatory cytokines and chemokines in the lung following viral infection comprises administering to subject in need thereof a pharmaceutical composition comprising an effective amount of prostacyclin/prostaglandin analog or beraprost or pharmaceutically acceptable salt thereof. In some examples, pro-inflammatory cytokines and chemokines are selected from IL-1α, IL-β, IL-2, IL-4, IL-6, IL-7, IL-8, IL-10, IL-12, INF-γ, TNF-α, IP-10, MCP-1, MIP-1, RANTES, and combinations thereof. In some examples, the pharmaceutical composition inhibits the release of pro-inflammatory cytokines and/or chemokines in peripheral blood lymphocytes, human alveolar epithelial cells, and bronchial epithelial cells.

In some examples, a method of treating a severe respiratory illness due to viral infection and characterized by upregulation of IL-2, IL-4, IL-6, IL-7, IL-8, and IL-10 comprises administering to subject in need thereof a pharmaceutical composition comprising an effective amount of prostacyclin/prostaglandin analog or beraprost or pharmaceutically acceptable salt thereof. In some examples, the severe respiratory illness is caused by a viral infection, a corona virus infection, a SARS-CoV infection, a MERS-CoV infection, or a SARS-CoV-2 infection.

In some examples, a method of treating a viral disease associated with the induction of one or more of IL-1α, IL-β, IL-2, IL-4, IL-6, IL-7, IL-8, IL-10, IL-12, INF-α, INF-γ, TNF-α, IP-10, MCP-1, MIP-1, RANTES can comprise administering to a subject in need thereof a pharmaceutical composition comprising an effective amount of prostacyclin/prostaglandin analog or beraprost or pharmaceutically acceptable salt thereof. In some examples, the viral disease is a severe respiratory illness caused by a viral infection, a corona virus infection, a SARS-CoV infection, a MERS-CoV infection, or a SARS-CoV-2 infection.

In some examples, a method of downregulating the levels of cytokines selected from IL-2, IL-4, IL-6, IL-7, IL-8, and IL-10 that are associated with viral infection, the method can comprise administering to a subject in need thereof a pharmaceutical composition comprising an effective amount of prostacyclin/prostaglandin analog or beraprost or pharmaceutically acceptable salt thereof. In some examples, the pharmaceutical composition downregulates the levels of cytokines in peripheral blood lymphocytes, human alveolar epithelial cells, and bronchial epithelial cells. In some examples, the viral infection is a corona virus infection, a SARS-CoV infection, a MERS-CoV infection, or a SARS-CoV-2 infection.

Subjects to be Treated

The subject can generally be any mammal. Examples of subjects include a non-human primate, a human, a dog, a cat, a mouse, a rat, a cow, a goat, a sheep, a rabbit, a horse, and a pig. In some examples, the subject is a human. The terms "subject," "individual" or "patient" are used interchangeably and as used herein are intended to include human and non-human animals. Non-human animals include all vertebrates, for example, mammals and non-mammals, such as non-human primates, sheep, dogs, rats, cats, cows, horses, chickens, amphibians, and reptiles. Examples of mammals include non-human primates, sheep, dogs, cats, cows, and horses. In some examples, the subject is a human or humans. The methods are suitable for treating humans having a viral infection or disease. The subject may be symptomatic or asymptomatic.

Manufacture of Medicaments

Additional examples include the use of at least one prostacyclin/prostaglandin analog in the manufacture of a medicament for the treatment of a viral infection. The prostacyclin/prostaglandin analog can be any of the analogs described above. For example, the analog can be beraprost or a or a pharmaceutically acceptable salt thereof. Additional examples include beraprost sodium salt, BPS-314d, BPS-3141, BPS-315d, BPS-3151, or combinations thereof. In one specific example, the beraprost is BPS-314d (esuberaprost sodium salt). The viral infection can generally be any viral infection. Specific examples of viral infections include comprises infection by SARS-CoV, MERS-CoV, or SARS-CoV-2. In one specific example, the viral infection is infection by SARS-CoV-2. For example, the use of BPS-314d (esuberaprost sodium salt) in the manufacture of a medicament for the treatment of a viral infection is described.

Kits

In additional examples, kits are provided for treating viral infection in a subject. The kits can comprise a first container containing a pharmaceutical composition comprising at least an effective amount of prostacyclin/prostaglandin analog or beraprost or pharmaceutically acceptable salt thereof; and instructions for the administration of the pharmaceutical composition to the subject. Any of the above-described pharmaceutical compositions can be included in the kit. The kit can further comprise a second container, a third container, and so on containing additional pharmaceutical compositions or other active ingredients. In some examples, the first container can contain a pharmaceutical composition, and the second container can contain at least one solvent or solvents to be mixed with the pharmaceutical composition before orally administering to the subject according to the instructions. In an example, the kit can comprise a first container containing beraprost or a pharmaceutically acceptable salt thereof, and a second container containing an aqueous solvent. In other examples, the second container can contain at least one antiviral compound, or at least one antimalarial compound.

EXAMPLES

Example 1: A Randomized, Double-Blind, Multiple Ascending Dose, Study to Assess the Safety and Efficacy of GP1681 Plus Standard of Care Compared to Standard of Care Alone in Adult Patients Hospitalized for COVID-19

Study Objectives: The Stage 1 objective is to determine a maximum safe dose to initiate GP1681 therapy in Stage 2. The primary objective is to determine the effect of GP1681 on the clinical and associated pro-inflammatory course of patients hospitalized with COVID-19 and the secondary objectives are to: (i) confirm the safety of GP1681 when administered for 7 days; (ii) determine the effect of GP1681 on clinical biomarkers associated with COVID-19; and (iii) examine the effect of GP1681 on cytokine biomarkers of immune function.

Study Design: The trial will be conducted as a multi-center, double-blinded, randomized, placebo-controlled, phase 2 study of GP1681 as compared to placebo in patients hospitalized for COVID-19 infection in two stages. After determination of eligibility and signing informed consent, patients receiving standard of care will be randomized to receive GP1681 or matching placebo for a total of 7 days. Concomitant standard of care therapies including anti-viral drugs are allowed but concomitant immunomodulatory therapies are prohibited. Following in-hospital drug treatment, patients can be discharged at the discretion of the investigator if it is determined that their COVID-19 has resolved. For study purposes, follow-up visits will be conducted at Days 8 and 14 (Follow-Up Visits) following first investigational drug dose and again at Day 28 post first dose of medication (Final Visit).

Stage 1—Dose Escalation/Biomarker Evaluation. Four cohorts will be enrolled sequentially. In each cohort, 9 patients receiving standard of care will be randomly assigned to receive either GP1681 or placebo in a 2:1 ratio. A total of up to 36 patients will be enrolled in Stage 1. Dosing will begin at 7.5 µg/day in divided doses (2.5 µg q8h) and escalate GP1681 to µg/day (5 µg q8h), to 30 µg/day (10 µg q8h) and then to 45 µg/day (15 µg q8h) in divided doses. Patients receiving treatment in Cohorts 2, 3 and 4 who do not tolerate the treatment they are receiving may decrease to the next lower Cohort treatment. A Data Safety Monitoring Board (DSMB) will review blinded safety data in an ongoing manner and no pause in study enrollment will be required between cohorts. The DSMB may determine that the maximum safe dose has been reached and that no further dose escalation is required. Patients to be randomized in a Cohort treatment that has a dose that is greater than the maximum safe dose identified by the DSMB will be enrolled into Stage 2.

Stage 2: Completion of Efficacy Enrollment. After the successful completion of Stage 1, the remainder of the patients in Stage 2 (at least 164 patients) will be enrolled and randomized in a 1:1 ratio of 45 µg/day (or the maximum safe dose) of GP1681 or Placebo. Individual patient treatment duration: 7 days.

GP1681 oral solution every 8 hours (q8h) or matching Placebo

Stage 1

Target doses for the first four cohorts of patients will be as follows:

Cohort 1: 2.5 µg q8h (Total daily dose 7.5 µg)
Cohort 2: 5.0 µg q8h (Total daily dose 15 µg)
Cohort 3: 10.0 µg q8h (Total daily dose 30 µg)

Cohort 4: 15.0 μg q8h, (Total daily dose 45 μg), or maximum tolerated dose

The DSMB will be empowered to modify the dose escalation schedule and/or the final dose in Cohort 4 (and Stage 2) if it is determined to be advisable due to ongoing safety results.

Stage 2:

15.0 μg q8h, (Total daily dose 45 μg), or maximum safe dose identified in Stage 1.

Food has a positive effect on oral absorption of GP1681. All doses of GP1681 should be administered with at least a light snack to insure adequate absorption. For patients receiving GP1681 via tube feeding, 100 mL of a nutrient drink may be substituted for food consumption.

Patients who experience intolerable side effects (e.g., headache, flushing or diarrhea) from GP1681 or matched placebo may receive the next lower dose investigated in Stage 1 rather than discontinuing treatment.

Preparation of Solution

Doses can be administered as an aqueous liquid formulation. 5 mg beraprost sodium salt BPS-314d (esuberaprost; GP1681) as a white crystalline solid powder is reconstituted with 10% w/v polyethylene glycol 400 (PEG 400) in phosphate buffered saline, pH 7.4 (PBS) aqueous vehicle. Secondary dilutions will be made with reconstitute drug and diluent to form the dosing solution that will be administered to a study participant. The solution can be stored in a refrigerator at 2-8° C.

Selection of Test Subjects

Total subjects for two stages are approximately 200 adults having the COVID19 disease are selected for treatment. Stage 1 has about 9 patients for each of 4 cohorts in dose escalation groups. Stage 2, the expansion cohort, has at least 164 subjects. Test subject in both stages will be randomized 1:1 (GP1681:placebo).

Inclusion criteria include 1) Male or female patients ≥18 years of age at the time of signing the informed consent form; 2) Patients hospitalized due to COVID-19 confirmed by WHO criteria: Positive PCR for SARS-CoV-2 from any specimen; Have a chest x-ray (CXR) or chest computed tomography (CT) scan consistent with viral pneumonia or acute respiratory distress syndrome (ARDS), i.e., ground glass appearance, local patchy or bilateral patchy shadowing, or bilateral reticular nodular opacities; and Peripheral capillary oxygen saturation (SpO2)<94% or PaO2/FiO2<300 mmHg at initial presentation/hospital admission or after hospital admission before enrollment; 3) Women of childbearing potential who agree to use a highly effective method of contraception for 3 months after the last dose of study drug; 4) Male patients who agree to effective contraception during the study and for 7 days following the last drug administration; 5) Patients who are able to provide written informed consent prior to the pre-dose procedures; or patients who have a legal representative capable of providing informed consent on their behalf.

Exclusion criteria include: 1) Patients who have been exposed to any immune modulator within 30 days prior to enrollment (any drug, with or without marketing approval) or who are currently being treated with an immune modulator. 2) History of known, or suspected to have, moderate or severe renal impairment (actual or estimated creatinine clearance <30 mL/min); 3) Known active bacterial co-infection; 4) Known active neoplasm (other than basal cell skin cancer); 5) Alanine Aminotransferase (ALT) or aspartate aminotransferase (AST) >10× upper limit of normal (ULN); 6) Absolute neutrophil count <1000/mL; 7) Platelet count <50,000/mL; 8) Cardiogenic shock, or severe current cardiac compromise defined as ejection fraction (EF)<35% (if known) or Cardiac output <3.5 L/min (if known); 9) Premorbid state, defined as, in the opinion of the investigator, that death is imminent within 24 hours despite treatment; 10) A history of bleeding diathesis or other bleeding disorders; 11) Patients currently receiving an inhaled vasodilator (e.g., prostacyclin, nitric oxide); 12) Presence of known Hepatitis B, C or HIV infection; 13) Presence of immunocompromised status due to previous organ transplant or use of immunosuppressive medical therapy within 30 days of screening; 14) Women who have a positive pregnancy test in the pre-dose examinations. Female patients who have documentation of either (a) or (b) (below) do not need to undergo a pregnancy test in the predose examinations: Postmenopausal (defined as cessation of regular menstrual periods for 2 years or more and confirmed by a follicle-stimulating hormone test) women—Women who are surgically sterile by hysterectomy, bilateral oophorectomy, or tubal ligation; 15) Any known drug allergy; 16) Women who are pregnant or within 2 weeks post-partum, or breast-feeding; 17) Patients who, in the opinion of the investigator, would be unlikely to comply with study procedures or are otherwise unsuitable for enrollment.

Primary and Secondary Endpoints

The co-primary endpoints will be the change from baseline to Day 8 in select(ed) cytokine concentrations (IL-6 and CRP).

The key secondary clinical endpoint will be determined as the time to clinical recovery as specified by 8 item ordinal scale. The ordinal scale is an assessment of the clinical status at the first assessment of a given study day. The scale is as follows: 1) Not hospitalized, no limitations on activities; 2) Not hospitalized, limitation on activities and/or requiring home oxygen; 3) Hospitalized, not requiring supplemental oxygen—no longer requires ongoing medical care; 4) Hospitalized, not requiring supplemental oxygen—requiring ongoing medical care (COVID-19 related or otherwise); 5) Hospitalized, requiring supplemental oxygen with nasal cannula (FIO2 about 40%); 6) Hospitalized, requiring supplemental oxygen with face mask (FIO2 about 50-60%); 7) Hospitalized, requiring supplemental oxygen with non-rebreather mask (FIO2 about 100%); 8) Hospitalized, on non-invasive ventilation with high flow (30 L/min) oxygen; 9) Hospitalized on invasive mechanical ventilation with low PEEP; 10) Hospitalized on invasive mechanical ventilation with high PEEP (according to ARDS-NET 2 criteria); 11) Hospitalized, on invasive mechanical ventilation with an inhaled vasodilator (prostacyclin or nitric oxide), or paralysis; 12) Hospitalized, on invasive mechanical ventilation with extracorporeal membrane oxygenation (ECMO); 13) Death.

The remaining secondary clinical endpoints will be as follows:

1. The change from baseline to other Days (Days 1, 3, 5, 14 and 28) in the primary endpoint.

2. Percentage of subjects who show clinical recovery, defined as a achieving a category 1, 2 or 3 in the 8-item scale (as defined in the Key Secondary Endpoint) at each visit 3. Percentage of subjects who show clinical improvement, defined as a 2-point improvement in the 8-item scale (as defined in the Key Secondary Endpoint) at each visit.

4. Time to clinical improvement as defined above.

5. National Early Warning Score (NEWS2) over time

6. Number of subjects with improved pulmonary function within 28 days, as defined by a change in Berlin definition for ARDS (None or mild, moderate, severe) from initiation 7. Duration (days) of ICU usage 8. Duration (days) of mechanical ventilation supply for all subjects (including deceased patients)

9. Duration (days) of mechanical ventilation supply among survivors, only

10. Duration of overall hospital stay

11. All-cause mortality

Safety Endpoint: Safety will be assessed by adverse event monitoring (including attribution of adverse events and serious adverse events), physical examination, vital signs and clinical laboratory testing.

Pharmacodynamic Endpoints: Level of COVID-associated Biomarkers: Change from baseline in lactate dehydrogenase (LDH), C-reactive protein (CRP), serum ferritin, serum procalcitonin, D-dimer, anti-nuclear antibodies (ANA), anti-phospholipid antibodies, and total lymphocyte count. Time Course of Cytokine Suppression: Levels of 27 cytokines will be assessed in nasal swabs and plasma/serum samples obtained once daily, prior to the morning dose. The cytokines to be included are: IL-1$\alpha$, IL-6, IL-15, TNF-$\beta$, IL-1$\beta$, IL-8, IL-17A/CTLA8, CCL2 (MCP-1), IL-2, IL-10, IFN-$\alpha$2, CCL3 (MIP-1$\alpha$), IL-4, IL-12 p70, IFN-gamma, CCL5 (RANTES), IL-5, IL-13, TNF-$\alpha$, CXCL10 (IP-10), IL-7, IL-9, VEGF-A, GCSF, GMCSF, bFGF, and PDGF. Both change from baseline and the time to maximal concentration will be assessed for these endpoints.

Subgroup analyses for all endpoints may include:

Patients on GP1681 without antiviral medication; Patients on both GP1681 and an(y) antiviral medication.

Patients Disease Status at entry

Presence of underlying Co-Morbidities

Product, Dose and Administration

GP1681 oral solution every 8 hours (q8h) or matching Placebo.

Stage 1—Target doses for the first four cohorts of patients will be as follows:

Cohort 1: 2.5 µg q8h (Total daily dose 7.5 µg)

Cohort 2: 5.0 µg q8h (Total daily dose 15 µg)

Cohort 3: 10.0 µg q8h (Total daily dose 30 µg)

Cohort 4: 15.0 µg q8h, (Total daily dose 45 µg), or maximum tolerated dose

The DSMB will be empowered to modify the dose escalation schedule and/or the final dose in Cohort 4 (and Stage 2) if it is determined to be advisable due to ongoing safety results.

Stage 2: 15.0 µg q8h, (Total daily dose 45 µg), or maximum safe dose identified in Stage 1.

Food has a positive effect on oral absorption of GP1681. All doses of GP1681 should be administered with at least a light snack to insure adequate absorption. For patients receiving GP1681 via tube feeding, 100 mL of a nutrient drink may be substituted for food consumption. Patients who experience intolerable side effects (e.g., headache, flushing or diarrhea) from GP1681 or matched placebo may receive the next lower dose investigated in Stage 1 rather than discontinuing treatment.

The aqueous solution of GP1681 will be dosed using a needle-less glass syringe and administered orally to the back of the throat.

Beneficial effects of treatment as compared to control.

Treatment of patients according to Examples 1-4 will show beneficial results relative to placebo control with both primary endpoints being met. Reductions in one or more key proinflammatory cytokines will correlate with patient improvement.

Example 2: Preparation of pharmaceutical composition as a tablet

Tablets are formed containing 1-10 ug active beraprost sodium salt BPS-314d (esuberaprost; GP1681). Conventional binders and inactive ingredients are included in the tablet. Placebo control tablets are formed using the same components but lacking the beraprost sodium salt.

Example 3: Administering Pharmaceutical Composition to Infected Subjects

The same inclusion criteria, exclusion criteria, and clinical endpoints as described in Example 1 will be followed. The tablet of Example 2 is orally delivered three times per day (TID) for 14 days, followed by an additional 28 days of safety follow-up for a total of approximately 42 days.

Example 4: Beneficial Effects of Treatment as Compared to Control

Treatment of patients according to Example 3 will show beneficial results relative to placebo control with both primary endpoints being met. Reductions in one or more key proinflammatory cytokines will correlate with patient improvement.

Example 5: Evaluating Different Dosages of GP1681

A trial will be performed to compare high and low dosages of GP1681. A group of 150 COVID-19 patients will be used (60 patients treated with a high dose of GP1681, 60 patients treated with a low dose of GP1681 and 30 patients with standard of care treatment). The same selection criteria and the same primary and secondary endpoints as described above in Example 1 will be used.

The solution of Example 1 above will be used. Dilutions will be performed to arrive at a high dose concentration and a low dose concentration. The aqueous formulations of GP1681 will be dosed using a needle-less glass syringe and administered orally to the back of the throat.

Example 6: Beneficial Effects of Treatments as Compared to Control

Treatment of patients according to Example 5 will show beneficial results relative to placebo control with both primary endpoints being met. Reductions in one or more key proinflammatory cytokines will correlate with patient improvement.

Example 7: Healthy Normal Volunteer Trial Design

A three cohort trial design will be used to evaluate GP1681 against placebo control. A patient population of 24 individuals will be assembled. The volunteers will be healthy males and females, from 18 to 65 years old, having a minimum body weight of 45 kg to 100 kg, and having a body mass index (BMI) of 18 kg/m$^2$ to 30 kg/m$^2$. Criteria for evaluation will include safety and tolerability/viral reactivation, pharmacokinetic, and pharmacodynamics (cytokines).

Cohort 1 will have screening and randomization 3:1 (n=8). One group will receive 15 micrograms/day GP1681 (5 micrograms every eight hours (Q8h)) for seven days, while the control group will receive a matching placebo for seven days. Afterwards there will be a 14 day follow-up with DEC review.

Cohort 2 will follow the same procedure, except that 30 micrograms/day GP1681 (10 micrograms every eight hours (Q8h)) will be used.

Cohort 3 will follow the same screening and randomization procedure. GP1681 will be administered at 45 micrograms/day (15 micrograms three times a day (TID)) for three days, then 60 micrograms/day (20 micrograms three times a day (TID)) for four days will be used.

Example 8: COVID-19 Phase 2 Trial Design

A patient population of 150 individuals will be assembled. The patients will be male or female patients at least 18 years old and having a common COVID-19 related symptoms score of at least 2 in any combination of items. They will have a positive outpatient test for SARS-CoV-2 infection, will not require hospitalization, and will be discharged to outpatient status. These patients will be at high risk of progression to severe SARS-CoV-2 infection.

Key endpoints will be change from baseline to last day of treatment in one or more selected cytokines and biomarker concentrations (such as IL-6 and CRP), as well as incidence of hospitalization for SARS-CoV-2 infection through day 28.

Patients will be screened and randomized 1:1 (n=150). The control group (n=75)) will receive matching placebos (three times a day; TID). The treatment group will receive GP1681 for a total of seven days: 30 micrograms per day (10 micrograms three times a day (TID)) for one day, 45 micrograms per day (15 micrograms three times a day (TID)) for 1 day, and 60 micrograms per day (20 micrograms three times a day (TID)) for five days.

Both groups will have a 3 weeks post-treatment follow-up, and a cancer follow-up at 3 and 6 months post-treatment.

Example 9: Stability and Formulation Studies

GP1681 in 10% (w/v) polyethylene glycol (PEG) 400 in calcium and magnesium free phosphate buffered saline (PBS), pH 7.4 was used for evaluation by ultra-high performance liquid chromatography (UHPLC; Agilent 1290 UHPLC instrument).

Dosing formulations of GP1681 (0, 0.01, 0.03, and 0.05 mg/mL) in 10% (w/v) PEG 400 in calcium and magnesium free PBS, pH 7.4 were collected and analyzed by UHPLC to assess accuracy of the preparation. Aliquots from the top, middle and bottom of the formulations were collected and analyzed to assess homogeneity of the formulations. The dosing formulations were diluted to bring the test article concentration to a suitable level within the calibration range. The samples were initially analyzed on the day of preparation. However, due to unacceptable results observed, the backup samples (stored at −10 to −30° C.) were analyzed five days later. A sample of vehicle dosing solution was also analyzed to verify that it did not contain test article.

The concentration of GP1681 was calculated by reference to the solvent standard solutions prepared and analyzed concurrently with the dosing formulations. All solvent standard curves met the acceptance criteria.

All primary dosing formulations analyzed were above the acceptance criteria of 80.0-120.0% of target concentration but had ≤10.0% RSD. In the backup sample analysis, the 0.01 and 0.03 mg/mL dosing formulations again were above the acceptance criteria of 80.0-120.0% of target concentration, but the 0.05 mg/mL formulation was within the acceptable range. All backup samples had ≤10.0% RSD. No test article was detected in the vehicle control (VC) samples.

Stability of the dosing formulations was determined by storing the middle aliquots of the high and low primary dose formulation samples in the Definitive Assay at room temperature for 3.7 hours and reanalyzing as described above. The results met the acceptance criterion of 90-110% of the concentration determined at T=0.

GP1681 in 10% (w/v) PEG 400 in calcium and magnesium free PBS, pH 7.4, at concentrations of 0.0319 and 0.0596 mg/mL, was stable at room temperature for at least 3.7 hours.

The results of the analysis indicate that the actual mean concentrations of the analyzed formulation samples, 0.01, 0.03 and 0.05 mg/mL, were between 110.3 and 317.7% of target with ≤10.0% RSD. All formulations were found to be above the acceptable range for concentration (80.0 to 120.0% of target) with the exception of the 0.05 mg/mL formulation in the backup sample analysis, which was within the acceptable range. All samples had ≤10.0% RSD. No test article was detected in the vehicle control samples.

Although these results indicate that the formulations were homogeneous, the actual concentrations of the majority of the samples analyzed were higher than expected. An analysis investigation was conducted; however, no cause for the unacceptable results could be attributed to preparation of the samples for analysis or analysis of the samples by the Analytical Chemistry Laboratory.

GP1681 in 10% (w/v) PEG 400 in calcium and magnesium free PBS, pH 7.4, at concentrations of 0.0319 and 0.0596 mg/mL, was stable at room temperature for at least 3.7 hours.

Example 10: Functional Binding Analysis to Multiple Human Prostanoid Receptors

DiscoverX cell-based ligand binding assays were performed in the PathHunter beta-arrestin (EP1, EP2, EP3, EP4, FP, IP, and TP receptors) or cAMP Hunter™ (DP receptor) cell lines.

Results revealed new information on the prostanoid receptor binding characteristics of GP1681. GP1681 does not bind the EP2, FP, or TP receptors. GP1681 demonstrated the highest receptor binding affinity for the IP receptor, similar to what had been observed with GP1681's parent compound, Beraprost. Beraprost was used as a positive control specifically for the IP receptor assay. Beraprost demonstrated about 4-fold lower affinity as compared to GP1681 for the IP receptor, also as observed before. This difference in affinity or EC50 values between Beraprost and GP1681 is expected given that GP1681 is a single isomer of a racemic mixture of four isomers. The EP1, EP3, and EP4 receptor results indicated approximately equivalent affinities (difference less than 5-fold) while the DP receptor had the lowest affinity binding for the activated receptors. The following table lists the summary of the results, where NB indicates no observed binding. Procedural details are described after the table.

| Receptor | Molecule | Gene | Assay | EC50 (uM) |
| --- | --- | --- | --- | --- |
| DP1 | GP1681 | PTGDR | cAMP | 1.33 |
| EP1 | GP1681 | PTGER1 | β-Arrestin | 7.81 |
| EP2 | GP1681 | PTGER2 | β-Arrestin | NB |
| EP3 | GP1681 | PTGER3 | β-Arrestin | 5.39 |
| EP4 | GP1681 | PTGER4 | β-Arrestin | 18.06 |
| FP | GP1681 | PTGFR | β-Arrestin | NB |
| IP | Beraprost | PTGIR | β-Arrestin | 0.436 |
| IP | GP1681 | PTGIR | β-Arrestin | 0.110 |
| TP | GP1681 | TBAX2R | β-Arrestin | NB |

Receptor binding studies were performed in either the PathHunter® b-Arrestin (EP1, EP2, EP3, EP4, FP, IP, and TP receptors) or cAMP Hunter™ (DP receptor) cell lines. A 10 mM working stock of GP1681 was created in 1×PBS, pH 7.4. All assays were carried out in duplicate with 10 individual concentrations of GP1681. A three-fold dilution series of GP1681 was established for the initial or pilot experiment with a starting concentration of 4 uM (starting concentration was chosen based on previous Gemmus Pharma preclinical experimental results). To induce the reporter response from resultant signal transduction through receptor binding, GP1681 samples were added to the appropriate reporter cell lines which had been plated 18-24 hours before assay start.

GP1681 was incubated with cells lines at either 37° C. or room temperature, for 90-180 minutes (temperatures and incubation times are all dependent on established optimized procedures for each receptor cell line) after which cell wells were processed and signal production detected. Positive controls were included for each receptor—PGD2 (DP receptor), PGE2 (EP1-4 receptors), Cloprostenol (a synthetic analogue of prostaglandin F2α (PGF2α)—FP receptor), Beraprost (prostacyclin agonist—IP receptor), and I-BOP (thromboxane receptor agonist—TP receptor). Vehicle only controls (PBS, pH 7.4) were also included for each receptor cell line. Receptor binding activity was analyzed using CBIS data analysis suite (ChemInnovation, CA). The percentage of activity was calculated using the following formula: % Activity=100%×(mean RLU of test sample−mean RLU of vehicle control)/(mean MAX control ligand−mean RLU of vehicle control). Dose curves were performed and EC50 values determined. The data from Run 1 is presented in the following table, with DP1 receptor evaluated in the Hit-Hunter cAMP assay cell line, and the remaining evaluated in the PathHunter β-Arrestin assay cell line.

| Receptor | Molecule | Gene | Assay | EC50 (uM) |
|---|---|---|---|---|
| DP1 | Control (PDG2) | PTGDR | cAMP | 0.0022 |
| DP1 | GP1681 | PTGDR | cAMP | 1.35 |
| EP1 | Control (PGE2) | PTGER1 | β-Arrestin | 0.0049 |
| EP1 | GP1681 | PTGER1 | β-Arrestin | 1.08 |
| EP2 | Control (PGE2) | PTGER2 | β-Arrestin | 1.24 |
| EP2 | GP1681 | PTGER2 | β-Arrestin | NB |
| EP3 | Control (PGE2) | PTGER3 | β-Arrestin | 0.0066 |
| EP3 | GP1681 | PTGER3 | β-Arrestin | 1.827 |
| EP4 | Control (PGE2) | PTGER4 | β-Arrestin | 0.00044 |
| EP4 | GP1681 | PTGER4 | β-Arrestin | 1.740 |
| FP | Control (cloprostenol) | PTGFR | β-Arrestin | 0.011 |
| FP | GP1681 | PTGFR | β-Arrestin | NB |
| IP | Control (Beraprost) | PTGIR | β-Arrestin | 0.436 |
| IP | GP1681 | PTGIR | β-Arrestin | 0.110 |
| TP | Control (I-BOP) | TBAX2R | β-Arrestin | 0.032 |
| TP | GP1681 | TBAX2R | β-Arrestin | NB |

Four different receptor results of GP1681, the DP, EP1, EP3, and EP4 receptor cell lines, did not begin at high enough starting concentrations to achieve the necessary sigmoidal curve required for confidence in determined EC50 values. The four assays were repeated with a higher starting concentration.

The second experimental run of the receptor binding assay was performed with these last four cell lines including GP1681 and their respective positive and negative (vehicle, PBS pH 7.4) controls. A 10 mM GP1681 working stock was again created in 1×PBS, pH 7.4. A three-fold serial dilution scheme was again used for GP1681 samples, starting this time at a concentration of 500 μM. The remainder of the second experimental run was performed in the same manner as run 1. Results are shown in the following table, with DP1 receptor evaluated in the HitHunter cAMP assay cell line, and the remaining evaluated in the PathHunter β-Arrestin assay cell line.

| Receptor | Molecule | Gene | Assay | EC50 (uM) |
|---|---|---|---|---|
| DP1 | Control (PDG2) | PTGDR | cAMP | 0.0012 |
| DP1 | GP1681 | PTGDR | cAMP | 1.33 |
| EP1 | Control (PGE2) | PTGER1 | β-Arrestin | 0.0063 |
| EP1 | GP1681 | PTGER1 | β-Arrestin | 7.81 |
| EP3 | Control (PGE2) | PTGER3 | β-Arrestin | 0.0076 |
| EP3 | GP1681 | PTGER3 | β-Arrestin | 5.39 |
| EP4 | Control (PGE2) | PTGER4 | β-Arrestin | 0.0007 |
| EP4 | GP1681 | PTGER4 | β-Arrestin | 18.06 |

Example 11: Confirmation of GP1681 Mechanism of Action Via EP4 Receptor

This Example describes antagonist assay experiments performed with known EP4 receptor inhibitors. Agonist controls and antagonist binding studies were performed in the PathHunter® β-Arrestin PTGER4 (EP4) cell lines. The PathHunter® β-Arrestin assay monitors activation by bound ligands of a GPCR in a homogenous, non-imaging assay format using Enzyme Fragment Complementation (EFC) with β-galactosidase (β-Gal) as the functional reporter. A fresh 10 mM working stock of GP1681 was created in the vehicle (1×PBS, pH 7.4). Prior to setting up the GP1681-antagonist assays, the parameters of the GP1681 agonist assay were optimized for most efficient cellular activation and expression of the reporter molecule via GP1681 receptor (PTGER4) binding. Two different cell densities (5K vs 7.5K) and incubation temperatures (room temperature and 37 C) were evaluated in standard agonist format. For agonist control assays, data was normalized to the maximal and minimal response observed in the presence of control ligand and vehicle. Three-fold dilution series of GP1681 or PGE2 (10 individual concentrations) were added to the PTGER4 cells which had been plated 18-24 hours before assay start at the indicated two different densities. GP1681/PGE2 were incubated with PTGER4 cells at either 37° C. or room temperature, for 90-180 minutes after which cell wells were processed and signal production detected. Vehicle only controls (1×PBS, pH 7.4) were also included for each receptor cell line. Receptor binding activity was analyzed using CBIS data analysis suite (ChemInnovation Software, Inc., San Diego, CA, USA).

The percentage of activity was calculated using the following formula: % Activity=100%×(mean RLU of test sample−mean RLU of vehicle control)/(mean MAX control ligand−mean RLU of vehicle control). Dose curves were performed and EC50 values determined. The EC50 values for each variable cell density and incubation temperature for both PGE2 and GP1681 are summarized in the table below. In all rows, the assay was Arrestin, the assay target was PTGER4, and the result type was EC50 for all agonists, and IC50 for all antagonists. NI indicates no inhibition, N is number of replicates, K is cell density, and RT is room temperature.

| Compound | Assay | RC50 (μM) | Condition |
|---|---|---|---|
| PGE2 | Agonist | 0.00093145 | N = 2, 5K 37C |
| PGE2 | Agonist | 0.00060643 | N = 2, 5K RT |
| PGE2 | Agonist | 0.00076703 | N = 1, 5K 37C |

-continued

| Compound | Assay | RC50 (µM) | Condition |
|---|---|---|---|
| PGE2 | Agonist | 0.00054419 | N = 1, 5K RT |
| PGE2 | Agonist | 0.0007104 | N = 1, 7.5K 37C |
| PGE2 | Agonist | 0.00051918 | N = 1, 7.5K RT |
| PGE2 | Agonist | 0.00083707 | N = 2, 7.5K 37C |
| PGE2 | Agonist | 0.00047652 | N = 2, 7.5K RT |
| GP1681 | Agonist | 23.44445 | N = 1, 5K 37C |
| GP1681 | Agonist | 12.73884 | N = 1, 5K RT |
| GP1681 | Agonist | 22.01658 | N = 1, 7.5K 37C |
| GP1681 | Agonist | 14.7693 | N = 1, 7.5K RT |
| GP1681 | Agonist | 16.21848 | N = 2, 5K 37C |
| GP1681 | Agonist | 16.06054 | N = 2, 5K RT |
| GP1681 | Agonist | 17.9523 | N = 2, 7.5K 37 |
| GP1681 | Agonist | 11.09124 | N = 2, 7.5K RT |
| GP1681 | Agonist | 11.91873 | 5K 37C |
| AH 23848 (Ca salt) | Antagonist | NI | 5K 37C |
| CAY10580 | Antagonist | NI | 5K 37C |
| CJ-023423 | Antagonist | 0.02654544 | 5K 37C |
| E7046 | Antagonist | 0.01500894 | 5K 37C |
| GW 627368X | Antagonist | 0.04416518 | 5K 37C |
| L-161,982 | Antagonist | 0.03388285 | 5K 37C |

Based on both the results of the control molecule PGE2 and GP1681 EC50 values (Table 3), a cell density of 5K and incubation temperature of 37 C were chosen for the antagonist runs. The GP1681 binding curves were also used to determine the EC80 concentration of 45 µM which was used in the antagonist assays.

All antagonist assays were carried out in duplicate with 10 individual concentrations of one of six antagonist compounds (commercially available from Cayman Chemical; Ann Arbor, MI, USA). Compounds were chosen due to their published status as selective EP4 receptor binding partners and/or as established EP4 antagonists (some known competitive antagonists). For antagonist assays, data was normalized to the maximal and minimal response observed in the presence of EC80 ligand and vehicle. A three-fold dilution series of each compound was established with a parameters). Cells at a density of 5000 cells per well, plated 18-24 hours before assay start, were preincubated for approximately one hour with individual antagonist (serially diluted) samples followed by agonist challenge at the EC80 concentration. Incubation was at 37° C. for 90-180 minutes after which cell wells were processed for signal detection. Microplates were read following signal generation with a PerkinElmer Envision™ instrument (Waltham, MA, USA) for chemiluminescent signal detection. Vehicle only controls (PBS, pH 7.4) were also included for each antagonist run. Receptor binding activity was analyzed using CBIS data analysis suite (ChemInnovation, CA, USA). Data shown was normalized to the maximal and minimal response observed in the presence of control compound and vehicle respectively. Percentage inhibition was calculated using the following formula: % Inhibition=100%×(1−(mean RLU of test sample−mean RLU of vehicle control)/(mean RLU of EC80 control−mean RLU of vehicle control)). The IC50 values for each antagonist compound and GP1681 and PGE2 control EC50 values are summarized in the table below. EP4 antagonist AH23848, was identified in the IND 113037 study may proceed letter as an antagonist of interest for GP1681 characterization. The published IC50 values for AH23848 range between 3 µM-6 M. It is a known competitive antagonist for EP4 but is also widely recognized as a weak inhibitor. At the standard 10 µM top concentration AH23848 did not inhibit GP1681, indicating GP1681 has a greater affinity than the antagonist for the EP4 receptor. CAY10580 is not an EP4 antagonist. This molecule was included as a control molecule for Eurofins work. This compound, a prostaglandin (nonselective) agonist, did not inhibit activity of GP1681. A low level of complementary activity of CAY10580 was noted only at 3 and 10 µM concentrations. The other four remaining, potent EP4 antagonists all inhibited GP1681 activity within published IC50 values: CJ-023432 (IC50=35 mM), E7046 (IC50=13.5 nM), GW627368X (IC50=15 nM-60 nM), L-161,982 (IC50=30 nM-50 nM), all competitively inhibited GP1681 at IC50 values of 26.5 nM, 15 nM, 44.2 nM, and 33.9 nM, respectively. These data confirm through rigorous controls and antagonist compound selection the integrity of the GPCR antagonist assay and demonstrated robust and specific binding and subsequent activation of receptor-driven signaling pathway between GP1681 and the EP4 receptor.

The results of the agonist/antagonist data are summarized in the following table.

| Molecule | Assay Format | Gene/Receptor | Result Type | E/IC50 (µM) |
|---|---|---|---|---|
| PGE2 | Agonist | PTGER4 | EC50 | 0.000931 |
| PGE2 | Agonist | PTGER4 | EC50 | 0.000767 |
| GP1681 | Agonist | PTGER4 | EC50 | 23.44 |
| GP1681 | Agonist | PTGER4 | EC50 | 16.22 |
| GP1681 | Agonist | PTGER4 | EC50 | 11.92 |
| CAY10580 | Antagonist | PTGER4 | IC50 | NI |
| AH 23848 | Antagonist | PTGER4 | IC50 | NI |
| CJ-023423 | Antagonist | PTGER4 | IC50 | 0.02655 |
| E7046 | Antagonist | PTGER4 | IC50 | 0.015 |
| GW 627368X | Antagonist | PTGER4 | IC50 | 0.0442 |
| L-161,982 | Antagonist | PTGER4 | IC50 | 0.03388 |

Example 12: Randomized, Double-Blind, Placebo-Controlled Study to Assess the Safety, Tolerability, Pharmacokinetics, and Pharmacodynamics of Multiple Ascending Doses of GP1681 in Healthy Adult Participants Study objectives: The primary objective is to evaluate the safety and tolerability of multiple oral doses of GP1681 as compared with placebo. The two secondary objectives are to (a) to evaluate the pharmacokinetics (PK) of GP1681; and (b) to evaluate the pharmacodynamics (PD) of GP1681 as demonstrated by changes in select cytokine levels in plasma.

The primary safety and tolerability endpoints are: (a) the frequency and severity of treatment-emergent adverse events (TEAEs), including clinically significant abnormal vital signs, ECGs, respiratory monitoring (including 02 saturation and spirometry), laboratory test results (including viral reactivation), cardiac telemetry results, and physical examination (PE) findings; and (b) the frequency and severity of adverse events of special interest (AESIs), including clinically significant changes from Baseline in coagulation parameters or platelets or persistent/recurrent symptomatic orthostatic hypotension.

The secondary plasma PK endpoints are: For initial (single) dosing (Day 1, post first dose): (a) Maximum observed concentration (Cmax); (b) time to maximum observed drug concentration (tmax); (c) apparent elimination half-life (t ½); (d) area under the drug concentration-time curve (AUC) from time zero to 8 hours postdose (AUC0-8); (e) AUC from time zero to the last measurable concentration within the first dosing interval based on actual times (AUC0-last); (f) AUC from time zero to infinity based on available first dosing interval measurable concentrations (AUC0-inf); (g) AUC from time t to infinity as a percentage of the total AUC (% AUCextrap); (h) apparent terminal elimination rate constant (kel); (i) apparent clearance (CL/F); and (j) apparent terminal volume of distribution (Vz/F). For multiple doses at steady state (SS) (Day 7 for Cohort 1 and 2, and Day 4 for Cohort 3): (a) maximum SS plasma concentration during a dosing interval (Cmax,ss); (b) time to maximum concentration at SS (tmax,ss); (c) lowest concentration in a dosing interval (Cmin,ss); (d) average concentration during a dosing interval (Cav,ss); (e) concentration at the end of the dosing interval (Ctrough); (f) AUC during a dosage interval (AUC0-tau) including AUC0-last, AUC0-inf, and AUC % extrap at SS; (g) AUC from time zero to 8 hours postdose (AUC0 8); (h) apparent terminal elimination rate constant at SS (kel,ss); (i) apparent clearance at SS (CL/Fss); (j) apparent terminal volume of distribution at SS (Vz/Fss); and (k) accumulation ratio (RA) for Cmax and AUCtau. The PD endpoints of the study are: actual values and change from Baseline in plasma cytokine levels.

The study is a double-blinded, randomized, placebo-controlled, multiple ascending dose (MAD) study of GP1681 as compared with placebo to be conducted in 3 sequential Cohorts of healthy volunteers. Participants enrolled into Cohorts 1 and 2 will received study drug (GP1681 or placebo) every 8 hours (q8h) within 30 minutes of eating a meal or snack. Cohort 3 participants will receive 3 doses daily of study drug (GP1681 or placebo) within 30 minutes of starting to eat a meal or snack (preferred 5 hours between the meals, ±30 minutes). Subjects in all cohorts will receive a total of 7 consecutive days (Day 1 to Day 7, inclusive) of dosing while domiciled at the clinical research unit (CRU).

Up to 24 participants will be enrolled into one of 3 MAD Cohorts (n=8 per Cohort). Participants will be administered GP1681 or placebo at a ratio of 3:1 per Cohort. Each Cohort will be evaluated for safety/tolerability by a Dose Escalation Committee (DEC) before beginning dosing in the next Cohort.

Participants enrolled into Cohorts 1 and 2 received study drug at 5 µg q8h for a total daily dose of 15 µg/day and 10 µg/dose, q8h a total daily dose of 30 µg/day respectively. Cohort 3 participants will initially receive 45 µg/day (15 µg/dose, TID with meal or snack, preferred 5 hours between the meals, [±30 minutes]) on Days 1, 2, and 3, and dosing will be escalated on Day 4 to 60 µg/day (20 µg/dose, TID with meal with meal or snack, preferred 5 hours between the meals [±30 minutes]) and will remain on this dose on subsequent treatment days (Days 5, 6, and 7). On Day 3, tolerability and safety parameters will be observed by the PI and if safe, the PI will escalate the dose to 60 µg/day as described. If Cohort 3 participants cannot tolerate their assigned dose at any time, subsequent dosing will continue at the last highest tolerated dose. Participants that do not tolerate the starting Cohort 3 dose (45 µg/day) may receive the 30 µg/day dose (10 µg/dose, TID with meal or snack, preferred 5 hours between the meals, [30 minutes].

| Cohort | Dose Level | Frequency | Total Daily Dose | Dosing Days |
|---|---|---|---|---|
| Cohort 1 | 5 µg | q8h | 15 µg | 7 consecutive days (Day 1 to Day 7, inclusive) |
| Cohort 2 | 10 µg | q8h | 30 µg | 7 consecutive days (Day 1 to Day 7, inclusive) |
| Cohort 3* | 15 µg | TID with meal or snack, (preferred 5 hours between the meals [± 30 minutes]) | 45 µg | Days 1, 2, 3 |
| | 20 µg | TID with meal or snack, (preferred 5 hours between the meals [± 30 minutes]) | 60 µg | Days 4, 5, 6 and 7 |

Participants will undergo a Screening period beginning up to 28 days prior to initial dose administration (Day 1). Participants will be required to sign an informed consent form (ICF) before undertaking any study specific procedures or assessments. Participants who are eligible for enrollment after Screening will be admitted to the CRU on the morning of Day −1 for Baseline assessments and review of inclusion and exclusion criteria to confirm eligibility prior to randomization. Participants will be monitored for safety and tolerability of study treatment, and blood and urine samples will be collected for the assessment of clinical laboratory (biochemistry, hematology, coagulation, and urinalysis) and PK/PD parameters at predefined time points pre- and postdose, as delineated in the Schedule of Assessments. Continuous cardiac telemetry will be conducted for 48 hours from Admission (Day −1) to the morning of Day 2. For all Cohorts, blood samples will be taken at Screening, prior to discharge on Day 8 and on Day 14 to test for the reactivation (i.e., quantitative PCR detection of viral load) of Epstein-Barr virus (EBV), herpes simplex virus (HSV), varicella zoster virus (VZV), and cytomegalovirus (CMV) in addition to direct questioning for emergence of skin lesions indicating viral reactivation. Participants will be discharged from the CRU on Day 8 (a minimum of 12 hours after the final dose) following successful completion of all specified study procedures and will return to the CRU for the end of study (EOS) follow-up visit on Day 14 (+2 days).

Up to 24 participants will be enrolled in the study. Participants who are enrolled but who do not receive any dose of study drug will be replaced and the replacement participant will receive the same treatment as the participant they are replacing. Participants who discontinue the study prior to the completion of dosing may be replaced at the discretion of the Sponsor.

Diagnosis and Main Criteria for Inclusion
Inclusion Criteria:
To be eligible for this study, participants must meet all of the following criteria:
Healthy male and female volunteers aged ≥18 to ≤65 years at the time of informed consent.
In good health as determined by medical history and PE at Screening and Admission to the CRU.
Must have a minimum body weight of ≥45 kg and ≤100 kg and a Body Mass Index (BMI) between 18 and 30 kg/m2, inclusive, at Screening.
Must have clinical laboratory values within normal range as specified by the testing laboratory, unless deemed not clinically significant by the Investigator or their delegate.
Negative test for drugs of abuse at Screening and Admission to the CRU.
Negative test for alcohol use (breathalyzer) at Screening and Admission to the CRU.

Women of childbearing potential (WOCBP) must use an acceptable, highly effective double barrier contraception from Screening until study completion, including the follow-up period. Double contraception is defined as a condom AND one other form of the following:

Established hormonal contraception (oral contraceptive pills [OCPs], long-acting implantable hormones, injectable hormones).

A vaginal ring or an intrauterine device (IUD).

Documented evidence of surgical sterilization at least 6 months prior to Screening (e.g., tubal occlusion, hysterectomy, bilateral salpingectomy, or bilateral oophorectomy for women or vasectomy for men [with appropriate post-vasectomy documentation of the absence of sperm in semen] provided the male partner is a sole partner).

Women not of childbearing potential must be postmenopausal for ≥12 months at Screening. Postmenopausal status will be confirmed through testing of follicle stimulating hormone (FSH) levels ≥40 IU/mL at Screening for amenorrheic female participants. Females who are abstinent from heterosexual intercourse will also be eligible.

Periodic abstinence (e.g., calendar, ovulation, symptothermal, post-ovulation methods) and withdrawal are not considered highly effective methods of birth control. Participants who practice complete abstinence as part of their usual and preferred lifestyle will be eligible.

Female participants who are in same sex relationships are not required to use contraception.

WOCBP must have a negative pregnancy test at Screening and prior to administration of the initial dose of study drug and must be willing to have additional pregnancy tests as required throughout the study.

Males must be surgically sterile (>30 days since vasectomy with no viable sperm), abstinent, or, if engaged in sexual relations with a WOCBP, his partner must be surgically sterile (e.g., tubal occlusion, hysterectomy, bilateral salpingectomy, bilateral oophorectomy) or the participant and his partner must be using an acceptable, highly effective double barrier contraceptive method from Screening until study completion, including the follow-up period. Acceptable methods of contraception include the use of condoms AND the use of an effective contraceptive for the female partner that includes: OCPs, long-acting implantable hormones, injectable hormones, a vaginal ring, or an IUD. Participants with same sex partners (abstinence from penile-vaginal intercourse) are eligible when this is their preferred and usual lifestyle.

Male participants must not donate sperm for at least 90 days after the last dose of study drug.

Must have the ability and willingness to attend the necessary visits to the CRU.

Must be willing and able to provide written informed consent after the nature of the study has been explained and prior to the commencement of any study procedures.

Exclusion Criteria:

A participant who meets any of the following criteria must be excluded from the study:

Pregnant or lactating at Screening or planning to become pregnant (self or partner) at any time during the study, including the follow-up period, until study completion.

Prior or ongoing medical conditions, medical history, physical findings, or laboratory abnormality that, in the Investigator's (or delegate's) opinion, could adversely affect the safety of the participant. Participants with history of the following will be excluded: irritable bowel syndrome, menorrhagia, fainting spells or dizzy spells or syncope, chronic abdominal or pelvic pain, hemoptysis, gastric ulcers, or anemia. Transient hemorrhage (e.g., infrequent epistaxis, normal menstrual bleeding, gingival bleeding, hemorrhoidal bleeding, etc.) would not preclude enrollment.

Presence of any underlying physical or psychological medical condition that, in the opinion of the Investigator, would make it unlikely that the participant will comply with the protocol or complete the study per protocol.

Any surgical or medical condition that could interfere with the absorption, distribution, metabolism, or excretion of the study drug.

Fever (body temperature >38° C.) or symptomatic viral or bacterial infection within 2 weeks prior to Admission to the CRU.

Any acute illness within 30 days prior to Admission to the CRU.

History of severe allergic or anaphylactic reactions, determined at the discretion of the Investigator.

Known or suspected intolerance or hypersensitivity to the IP, closely related compounds, or any of the stated ingredients.

History of malignancy except for non-melanoma skin cancer excised more than 2 years ago and cervical intraepithelial neoplasia that has been successfully cured more than 5 years prior to Screening.

Abnormal ECG findings at Screening or Admission that are considered by the Investigator to be clinically significant.

History or presence of a condition associated with significant immunosuppression.

History of life-threatening infection (e.g., meningitis) within 5 years prior to Screening.

Infections requiring parenteral antibiotics within the 6 months prior to Screening.

Vaccination with a live-attenuated vaccine within the 4 weeks prior to Screening through to the EOS.

Exposure to any significantly immunosuppressive drug (including experimental therapies as part of a clinical trial) within the 4 months prior to Screening or five half-lives, whichever is longer. Topical steroids are allowed at the discretion of the Investigator.

Positive hepatitis panel indicative of active, chronic, or past infection with hepatitis B (including hepatitis B surface antigen [HBsAg], hepatitis B core antibody [HBcAB]), or hepatitis C virus antibody (anti-HCV), or a positive human immunodeficiency virus (HIV) antibody screen.

A blood pressure (BP) value outside the specified range of 90 mm Hg to 160 mmHg (for systolic BP [SBP]) and 50 mm Hg to 95 mmHg for diastolic BP (DBP; both inclusive) at Screening or Admission (can be repeated once at Screening at the Investigator's discretion).

A history of substance abuse or dependency or history of recreational intravenous (IV) drug use over the last 5 years (by self-declaration).

Regular alcohol consumption defined as >14 alcohol units per week (where 1 unit=284 mL of beer, 25 mL of 40% spirit, or a 125 mL glass of wine) within 6 months of Screening. Participant is unwilling to abstain from alcohol beginning 48 hours prior to each visit and during the confinement period.

Regularly consume more than 8 cups (i.e., 2 L) daily of beverage containing caffeine and unable to abstain from caffeine- or xanthine-containing products for at least 24 hours prior to Admission to the CRU and during confinement.

Currently smoke (including tobacco, marijuana, e-cigarettes, vaping, nicotine gum, etc.) or have used such products within 2 weeks prior to Screening.

Have undergone major surgery or have donated blood within 12 weeks prior to the start of the study.

A history of bleeding diathesis or other bleeding disorders.

Use of any prescription medications/products (other than hormonal contraception: OCPs, long-acting implantable hormones, injectable hormones, vaginal ring, or IUD) within 30 days prior to Screening, unless reviewed and approved by the Investigator in consultation with the Sponsor. Simple analgesia (nonsteroidal anti inflammatory drug [NSAID] or paracetamol) may be permitted at the discretion of the Investigator.

Use of any over-the-counter (OTC), non-prescription preparations (including vitamins, minerals, phytotherapeutic/herbal/plant-derived preparations) within 14 days prior to Admission to the CRU.

A history of orthostatic hypotension or evidence of orthostatic hypotension at Screening that may make participation in the study inappropriate, as determined by the Investigator or delegate.

Investigational Product, Dosage and Mode of Administration:

GP1681

GP1681 as an aqueous liquid formulation will be orally administered using a needleless syringe to the back of the mouth. The diluent is 10% w/v polyethylene glycol 400 (PEG 400) in phosphate buffered saline, pH 7.4 (PBS). The IP will be provided in individual vials containing 5 mg of GP1681 as a powder along with accompanying diluent.

The first Cohort will receive the predefined dose of 5 µg q8h (15 µg/day).

Following review by the DEC, Cohort 2 will receive 10 µg q8h (30 µg/day). Cohort 3 participants will initially receive a dose of 45 µg/day (15 µg/dose, TID with meal) on Days 1, 2, and 3. Dosing will be escalated on Day 4 to 60 µg/day (20 µg/dose, TID with meal). The Cohort 3 dose level is subject to change following PI review of safety data on Day 3. If Cohort 3 participants cannot tolerate the dose, subsequent dosing will continue at last maximum tolerated dose. Participants that do not tolerate the initial 45 µg/day dose may receive a 30 µg/day TID with meal.

Duration of Treatment:

For each participant, the total duration of the study will be up to 16 days after Admission to the CRU (plus up to 28 days of Screening).

Reference Therapy, Dosage and Mode of Administration:

Placebo: The oral placebo will be 10% w/v PEG 400 in PBS pH 7.4, volume matched and administered in the same way as the IP.

Criteria for Evaluation:

Safety:

The safety and tolerability of multiple doses of GP1681 will be investigated using the following specific assessments: vital signs (SBP, DBP, pulse rate, body temperature, and respiratory rate), respiratory monitoring (including 02 saturation and spirometry), 12-lead ECG, clinical laboratory tests (hematology, biochemistry, coagulation, and urinalysis), cardiac telemetry, PE, viral reactivation (i.e., quantitative PCR detection of viral load and direct questioning for emergence skin lesions), and assessment of TEAEs and AESIs.

Pharmacokinetics:

Blood samples for plasma PK analysis of GP1681 will be collected predose and following oral administration of single (Day 1, post first dose) and multiple (days 2 through 7) doses of GP1681 according to the Schedule of Assessments.

Pharmacodynamics:

Blood samples for plasma cytokine level analysis will be collected pre- and postdose following oral administration of GP1681 according to the Schedule of Assessments. The cytokines to be included are:

Interleukins (IL): IL-1α, IL-1β, IL-2, IL-4, IL-5, IL-6, IL-7, IL-8, IL-9, IL-10, IL-12 p70, IL-13, IL-15, IL-17A/CTLA8

Granulocyte-macrophage colony-stimulating factor (GM-CSF)

Basic fibroblast growth factor (bFGF)

Interferon alpha 2 (IFN-α2)

IFN-γ

Vascular endothelial growth factor A (VEGF-A)

Platelet-derived growth factor (PDGF)

Tumor necrosis factor alpha (TNF-α)

TNF-β

Chemokine ligand 2 (CCL2) (MCP-1)

CCL3 (MIP-la)

CCL5 (RANTES)

CXCL10 (IP-10)

Granulocyte colony-stimulating factor (G-CSF)

Statistical Methods:

Statistical methods will be further outlined in a Statistical Analysis Plan (SAP). Procedures outlined in the SAP will supersede protocol-specified statistical methods in the event of divergence.

The number of participants was selected to allow for evaluation of safety/tolerability, PK, and PD in this study and is consistent with standards of practice for Phase 1 studies.

In general, descriptive statistics (e.g., arithmetic mean, standard deviation [SD], median, minimum, and maximum) will be calculated for continuous data by treatment as well as difference from Baseline for each applicable scheduled time point, when appropriate. Frequency summaries (e.g., number of observed and percentage of each category) will be applied for categorical data for each scheduled time point.

No formal hypothesis testing will be performed for this study.

Analysis Populations:

Participant inclusion in each population will be determined prior to the final analysis.

Safety Population: All participants who receive any amount of study drug (GP1681 or placebo) will be included in the Safety population. The Safety population will be used for the summaries of all safety assessments. Participants will be analyzed according to treatment received.

Pharmacokinetic Population: All participants who receive any amount of IP (GP1681) and have sufficiently evaluable concentration-time profiles to allow determination of at least one PK parameter will be included in the PK population. An evaluable PK profile will be determined at the discretion of the pharmacokineticist following examination of participants with dosing or protocol deviations that could potentially affect the PK profile. The PK population will be used for the summaries of all PK data.

Pharmacodynamic Population: All participants who receive at least one dose of study drug (GP1681 or placebo), who had at least one PD assessment at Baseline, and who had at least one PD assessment post Baseline.

Safety and Tolerability:

All AEs will be coded using the most current version of the Medical Dictionary for Regulatory Activities (MedDRA®). An AE data listing, including verbatim term, Preferred Term (PT), System Organ Class (SOC), treatment, severity, and relationship to study drug will be provided. The number of participants experiencing TEAEs will be summarized by SOC and PT. TEAEs will also be summarized by severity and by relationship to study treatment. The number of participants experiencing AESIs will be summarized by severity and by relationship to study treatment.

Laboratory evaluations (including viral reactivation), PEs, vital signs assessments, respiratory monitoring (including 02 saturation and spirometry), ECG parameters, and cardiac telemetry will be summarized for each scheduled visit. A summary of change from Baseline at each protocol-specified time point will also be presented, where applicable. Listings will also be provided for these parameters.

Concomitant medications will be coded using the most current version of the World Health Organization drug dictionary (WHO-DD). Concomitant medications will be listed by participant and summarized by Anatomical Therapeutic Chemical (ATC) and preferred name.

Medical history, PE, pregnancy test/FSH test, breast enlargement and vaginal mucification, urine drug screen/alcohol breath test, viral reactivation, and viral serology (HIV, Hepatitis B & C screen) results will be listed by participant.

Pharmacokinetics:

Plasma GP1681 concentrations, actual blood sampling times, and PK parameters will be listed by protocol-specified time point and will be summarized using descriptive statistics. Individual and mean GP1681 concentration time profiles will also be presented graphically.

Pharmacokinetic parameters will be computed from the individual plasma GP1681 concentrations by a non compartmental approach using Phoenix WinNonlin software, and will be estimated, as appropriate.

Pharmacodynamics:

Pharmacodynamic parameters (i.e., cytokine analyte plasma levels) and change from Baseline values will be listed and summarized descriptively by treatment arm for each time point.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

What is claimed is:

1. A method of treating a viral infection in a subject, the method comprising administering a pharmaceutical composition to the subject, wherein the pharmaceutical composition comprises at least an effective amount of esuberaprost or a pharmaceutically acceptable salt thereof,
   wherein the viral infection comprises infection by SARS-CoV, MERS-CoV, or SARS-CoV-2.

2. The method of claim 1, wherein the pharmaceutically acceptable salt is esuberaprost sodium salt.

3. The method of claim 1, wherein the viral infection comprises infection by SARS-CoV-2.

4. The method of claim 1, wherein the pharmaceutical composition further comprises at least one excipient, at least one filler, at least one disintegrant, at least one binder, at least one wetting agent, at least one lubricant, at least one glidant, at least one preservative agent, at least one flavoring agent, at least one antioxidant, or combinations thereof.

5. The method of claim 1, wherein the pharmaceutical composition is formulated as a tablet, capsule, granule, powder, liquid, suspension, gel, syrup, slurry, suppository, patch, nasal spray, aerosol, injectable, implantable sustained-release formulation, or mucoadherent film.

6. The method of claim 1, wherein the administering comprises topical delivery, subcutaneous delivery, intravenous injection (IV) delivery, intramuscular injection (IM) delivery, intrathecal injection (IT) delivery, intraperitoneal injection (IP) delivery, transdermal delivery, subcutaneous delivery, oral delivery, transmucosal oral delivery, pulmonary delivery, inhalation delivery, intranasal delivery, buccal delivery, rectal delivery, vaginal delivery, or combinations thereof.

7. The method of claim 1, wherein the administering comprises oral delivery.

8. The method of claim 1, wherein the esuberaprost or pharmaceutically acceptable salt thereof is present in a unit dose of the pharmaceutical composition in an amount of about 1 microgram to about 100 micrograms.

9. The method of claim 1, wherein the subject is a mammal.

10. The method of claim 1, wherein the subject is a primate, cat, dog, pig, cow, goat, horse, sheep, or rabbit.

11. The method of claim 1, wherein the subject is a human.

12. The method of claim 1, wherein the administering comprises delivering the pharmaceutical composition to the subject at an amount of esuberaprost or a pharmaceutically acceptable salt thereof at least about 0.1 microgram.

13. The method of claim 1, wherein the administering comprises delivering the pharmaceutical composition to the subject at an amount of esuberaprost or a pharmaceutically acceptable salt thereof at about 15 micrograms three times a day.

14. The method of claim 1, wherein the administering comprises delivering the pharmaceutical composition to the subject at a dosage of esuberaprost or a pharmaceutically acceptable salt thereof at about 20 micrograms three times a day.

15. The method of claim 1, wherein the administering comprises delivering the pharmaceutical composition to the subject at a dosage of esuberaprost or a pharmaceutically acceptable salt thereof at about 15 micrograms three times a day then at about 20 micrograms three times a day.

16. A method of treating a viral infection in a human subject, the method comprising orally administering a pharmaceutical composition to the subject three times per day (TID), wherein the pharmaceutical composition comprises about 15 µg to about 20 µg of BPS-314d (esuberaprost) for a daily dosage of about 45 µg to about 60 µg,
   wherein the viral infection comprises infection by SARS-CoV, MERS-CoV, or SARS-CoV-2.

* * * * *